US008957271B2

(12) United States Patent
Nesterenko et al.

(10) Patent No.: US 8,957,271 B2
(45) Date of Patent: *Feb. 17, 2015

(54) PROCESS TO MAKE OLEFINS FROM OXYGENATES

(75) Inventors: Nikolai Nesterenko, Nivelles (BE); Walter Vermeiren, Houthalen (BE); Giacomo Grasso, Brussels (BE); Sander Van Donk, Sainte Adresse (FR); Wolfgang Garcia, Waterloo (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 374 days.

This patent is subject to a terminal disclaimer.

(21) Appl. No.: 13/000,364

(22) PCT Filed: Jun. 24, 2009

(86) PCT No.: PCT/EP2009/057887
§ 371 (c)(1),
(2), (4) Date: Mar. 14, 2011

(87) PCT Pub. No.: WO2009/156433
PCT Pub. Date: Dec. 30, 2009

(65) Prior Publication Data
US 2011/0166303 A1 Jul. 7, 2011

(30) Foreign Application Priority Data

Jun. 25, 2008 (EP) .................................... 08158924
Mar. 3, 2009 (EP) .................................... 09154232

(51) Int. Cl.
*C07C 1/20* (2006.01)
*C07C 1/24* (2006.01)
(Continued)

(52) U.S. Cl.
CPC *B01J 38/12* (2013.01); *B01J 21/08* (2013.01); *B01J 21/16* (2013.01); *B01J 27/14* (2013.01);
(Continued)

(58) Field of Classification Search
CPC ............. C07C 1/20; C07C 1/24; B01J 29/18; B01J 29/40; B01J 29/65; B01J 29/85; B01J 37/10; B01J 37/28; B01J 2029/08; B01J 2029/81; B01J 2229/18; B01J 2229/36; B01J 2229/37
USPC .......... 585/638–640, 634; 502/60, 73, 85, 78, 502/79; 423/714
See application file for complete search history.

(56) References Cited

U.S. PATENT DOCUMENTS 5,171,921 A * 12/1992 Gaffney et al. ............... 585/653
6,303,839 B1 10/2001 Marker
(Continued)

FOREIGN PATENT DOCUMENTS

CN 1803738 A 7/2006
EP 0568913 A 11/1993
(Continued)

OTHER PUBLICATIONS

R.K. Sinnott, Coulson & Richardson's Chemical Engineering, Chemical Engineering Design, vol. 6, Fourth Edition, 2005, p. 50-54.*

(Continued)

*Primary Examiner* — In Suk Bullock
*Assistant Examiner* — Philip Louie

(57) ABSTRACT

The present invention relates to a process to make light olefins, in a combined XTO-OC process, from an oxygen-containing, halogenide-containing or sulphur-containing organic feedstock comprising:
a) providing a catalyst comprising zeolitic molecular sieves containing 10 member and larger channels in their microporous structure,
b) providing an XTO reaction zone, an OC reaction zone and a catalyst regeneration zone, said catalyst circulating in the three zones, such that at least a portion of the regenerated catalyst is passed to the OC reaction zone, at least a portion of the catalyst in the OC reaction zone is passed to the XTO reaction zone and at least a portion of the catalyst in the XTO reaction zone is passed to the regeneration zone;
c) contacting said oxygen-containing, halogenide-containing or sulphur-containing organic feedstock in the XTO reactor with the catalyst at conditions effective to convert at least a portion of the feedstock to form a XTO reactor effluent comprising light olefins and a heavy hydrocarbon fraction;
d) separating said light olefins from said heavy hydrocarbon fraction;
e) contacting said heavy hydrocarbon fraction in the OC reactor with the catalyst at conditions effective to convert at least a portion of said heavy hydrocarbon fraction to light olefins.

26 Claims, 8 Drawing Sheets

(51) Int. Cl.
| | |
|---|---|
| *B01J 38/12* | (2006.01) |
| *B01J 21/08* | (2006.01) |
| *B01J 21/16* | (2006.01) |
| *B01J 27/14* | (2006.01) |
| *B01J 29/18* | (2006.01) |
| *B01J 29/40* | (2006.01) |
| *B01J 29/65* | (2006.01) |
| *B01J 29/90* | (2006.01) |
| *B01J 37/10* | (2006.01) |
| *C07C 1/26* | (2006.01) |
| *C07C 1/32* | (2006.01) |
| *C10G 3/00* | (2006.01) |
| *C10G 9/00* | (2006.01) |
| *C10G 55/04* | (2006.01) |

(52) U.S. Cl.
CPC *B01J 29/18* (2013.01); *B01J 29/40* (2013.01); *B01J 29/65* (2013.01); *B01J 29/90* (2013.01); *B01J 37/10* (2013.01); *C07C 1/20* (2013.01); *C07C 1/26* (2013.01); *C07C 1/322* (2013.01); *C10G 3/44* (2013.01); *C10G 3/49* (2013.01); *C10G 9/00* (2013.01); *C10G 55/04* (2013.01); *C10G 3/62* (2013.01); *B01J 2229/16* (2013.01); *B01J 2229/186* (2013.01); *B01J 2229/36* (2013.01); *C10G 2400/20* (2013.01)

USPC ........... 585/638; 585/634; 585/639; 585/640; 502/60; 502/73; 502/85; 502/78; 502/79

(56) References Cited

U.S. PATENT DOCUMENTS

| | | | |
|---|---|---|---|
| 6,455,749 | B1 | 9/2002 | Vaughn |
| 7,384,883 | B2* | 6/2008 | Dath et al. ................ 502/85 |
| 7,722,825 | B1* | 5/2010 | Bozzano et al. ............ 422/141 |
| 2003/0078463 | A1* | 4/2003 | Martens et al. ............ 585/638 |
| 2005/0020436 | A1* | 1/2005 | Dath et al. ................ 502/64 |
| 2006/0149109 | A1* | 7/2006 | Ruziska et al. ............. 585/639 |
| 2006/0161035 | A1* | 7/2006 | Kalnes et al. ............. 585/639 |
| 2009/0216058 | A1* | 8/2009 | Dath et al. ................ 585/653 |

FOREIGN PATENT DOCUMENTS

| | | |
|---|---|---|
| EP | 1 797 951 A1 | 6/2007 |
| WO | 0166497 A | 9/2001 |
| WO | 03/020667 A1 | 3/2003 |
| WO | 2009016155 A | 2/2009 |

OTHER PUBLICATIONS

Office Action issued in Chinese Patent Application No. 200980124567.7, dated Mar. 14, 2014 (16 pages).

* cited by examiner

— 1 —

PROCESS TO MAKE OLEFINS FROM OXYGENATES

FIELD OF THE INVENTION

The present invention relates to a process to make olefins from heteroatomic organics and more precisely an XTO (organics to olefins) process combined with an OC (olefins conversion) process comprising a catalyst regeneration zone and such that at least a portion of the regenerated catalyst is passed to the OC reaction zone and at least a portion of the catalyst in the OC reaction zone is passed to the XTO reaction zone.

The limited supply and increasing cost of crude oil has prompted the search for alternative processes for producing hydrocarbon products. One such process is the conversion of oxygen-containing (by way of example methanol), halogenide-containing or sulphur-containing organic compounds to hydrocarbons and especially light olefins (by light olefins is meant $C_2$ to $C_4$ olefins) or gasoline and aromatics. In the present application said oxygen-containing, halogenide-containing or sulphur-containing organic compounds are also referred as "X". In the present application the conversion of said oxygen-containing (also referred as oxygenates), halogenide-containing or sulphur-containing organic compounds to hydrocarbons and especially light olefins is referred as XTO process. The interest in the XTO process is based on the fact that feedstocks, especially methanol can be obtained from coal, hydrocarbon residu's, biomass, organic waste or natural gas by the production of synthesis gas, which is then processed to produce methanol. The XTO process can be combined with an OC (olefins conversion) process to increase production of olefins. The XTO process produces light olefins such as ethylene and propylene as well as heavy hydrocarbons such as butenes and above. These heavy hydrocarbons are cracked in an OC process to give mainly ethylene and propylene. The XTO process is also known as MTO in case of methanol (methanol to olefins) process.

BACKGROUND OF THE INVENTION

U.S. Pat. No. 7,132,581 concerns processes for converting oxygenates to olefins that include a step of pretreating catalyst used in the conversion reaction. A fresh or regenerated metalloaluminophosphate molecular sieve, which is low in carbon content, is pretreated with an aldehyde. The aldehyde forms a hydrocarbon co-catalyst within the pore structure of the molecular sieve, and the pretreated molecular sieve containing the co-catalyst is used to convert oxygenate to an olefin product.

U.S. Pat. No. 7,057,083 relates to processes for converting oxygenates to olefins that include a step of pretreating molecular sieve used in the conversion reaction with a C4-C7 olefin composition, which contains one or more C4-C7 olefins. Fresh or regenerated molecular sieve, which is low in carbon content, is contacted or pretreated with the olefin composition to form a hydrocarbon co-catalyst within the pore structure of the molecular sieve, and the pretreated molecular sieve containing the co-catalyst is used to convert oxygenate to a lighter olefin product.

U.S. Pat. No. 6,844,476 describes a method for converting heavy olefins present in a product stream exiting a first reaction zone into light olefins and carbonaceous deposits on a catalyst without separation of the heavy olefins from the product stream exiting the first reaction zone. The method comprises creating the product stream exiting the first reaction zone, the product stream exiting the first reaction zone comprising the heavy olefins, moving the product stream exiting the first reaction zone to a second reaction zone without separation of the heavy olefins from the product stream exiting the first reaction zone, and contacting the product stream exiting the first reaction zone with the catalyst under conditions effective to form the light olefins, the contacting causing the carbonaceous deposits to form on at least a portion of the catalyst.

US20060161035 describes the average propylene cycle yield of an oxygenate to propylene (OTP) process using a dual-function oxygenate conversion catalyst is substantially enhanced by the use of a combination of:

1) moving bed reactor technology in the catalytic OTP reaction step in lieu of the fixed bed technology of the prior art;

2) a separate heavy olefin interconversion step using moving bed technology and operating at an inlet temperature at least 15° C. higher than the maximum temperature utilized in the OTP reaction step;

3) C2 olefin recycle to the OTP reaction step; and 4) a catalyst on-stream cycle time of 700 hours or less. These provisions hold the build-up of coke deposits on the catalyst to a level which does not substantially degrade dual-function catalyst activity, oxygenate conversion and propylene selectivity, thereby enabling maintenance of average propylene cycle yield for each cycle near or at essentially start-of-cycle levels.

U.S. Pat. No. 5,914,433 relates to a process for the production of light olefins comprising olefins having from 2 to 4 carbon atoms per molecule from an oxygenate feedstock. The process comprises passing the oxygenate feedstock to an oxygenate conversion zone containing a metal aluminophosphate catalyst to produce a light olefin stream. A propylene stream and/or mixed butylene is fractionated from said light olefin stream and butylenes and heavies cracked to enhance the yield of ethylene and propylene products. This combination of light olefin product and butylene and heavies cracking in a riser cracking zone or a separate cracking zone provides flexibility to the process which overcomes the equilibrium limitations of the aluminophosphate catalyst. In addition, the invention provides the advantage of extended catalyst life and greater catalyst stability in the oxygenate conversion zone. In said process the effluent of the riser cracking zone or the separate cracking zone is sent to the oxygenate conversion zone.

It has now been discovered a more efficient process to make light olefins, in particular propylene from oxygenates. This invention relates to a process including three zones: a XTO reaction zone containing catalyst wherein "X" (e.g. oxygenates) are converted into mainly light olefins, an OC reaction zone containing substantially the same catalyst wherein heavier olefins and optionally ethylene are cracked into other light olefins and a zone wherein the catalyst used in the other two zones is regenerated (the catalyst regeneration zone also referred as the regeneration zone). This invention relates to processes for converting oxygenates to olefins over a zeolite-based catalyst (in the XTO reaction zone) that include a step of primarily using the zeolite-based catalyst in the conversion reaction (the OC reaction zone) with a substantially olefinic feedstock, which contains one or more $C_2$-$C_{12}$ olefins, and forming by way of example 0.1 wt % or more of coke-like deposition on the molecular sieves. The main role of this hydrocarbons deposition is in selective deactivation of the non-selective acid sites. This contact of the molecular sieve with an olefinic feedstock could be performed in the presence or in absence of water and oxygenated compounds. In a most preferred embodiment, this contact is performed in the absence of water and oxygenated compounds. It was found that the primarily use (as a pre-treatment) of zeolite-based catalyst for the conversion of olefinic feedstock provides a catalyst with significantly improved catalyst performance for the MTO reaction in the XTO reaction zone. Without willing to be bound to any theory, it is believed that the effect consists in a selective poisoning of the non-selective acid sites at the external surface which are responsible typically for side-reaction, resulting in enhanced formation of paraffins and aromatics. In the present invention we are talking about selectively pre-deactivated catalyst in which the deposited coke has no catalytic activity as is in the case of coke co-catalyst on SAPO-type materials.

Another advantage in using the olefin compositions of this invention for the primarily use of zeolite-based catalyst is that this provides a way to reduce undesirable by-products in the overall conversion of oxygenates to olefins. Typically, heavier olefins such as the $C_4$-$C_7$ olefins are considered as undesirable by-products, because the value of those olefins are considerably lower than ethylene and propylene. Therefore, the by-products of the oxygenate to olefins reaction process can be used to enhance selectivity of the catalyst to provide the more desirable ethylene and propylene products.

ADVANTAGES OF THE PRESENT INVENTION

Perform the reaction in each operating zone under optimal conditions

Optimal catalyst selectivity by primarily use of the catalyst for olefin cracking Better heat integration between the different reactor zones Overall yield of light olefins higher because lower paraffin's and aromatic formation It is preferred that the catalyst in the three zones is in the fluidised state. This allows easy transport of catalyst from one zone to other zones.

The conversion of X is carried out in a separate zone (the XTO reaction zone) than the conversion of ethylene or C4-C7 hydrocarbons (the OC reaction zone). This allows optimising each reaction conditions separately. The conversion of X is a strongly exothermic conversion and is hence best performed in a fluidised bed with substantially homogenous temperature throughout the catalyst bed, wherein the temperature is regulated by injecting the feed at a temperature lower than the reaction temperature (cold feed serves as heat sink) or by cooling the catalyst by means of a catalyst cooler by raising steam in a heat exchanger. The conversion of C4-C7 olefins is on the contrary a strongly endothermic reaction. The heat of reaction can be provided by super-heating the feedstock so that the outlet temperature of the reactor is sufficiently high to obtain a sufficiently high conversion of the feedstock. The heat of reaction can also be provided by means of a high catalyst circulation rate at sufficiently high temperature to convert the feedstock. This can easily be done in a fluidised bed reactor with catalyst injection at the bottom of the reactor (inlet) with catalyst separation at the top of the reactor (outlet). Sufficiently hot catalyst can come from the regenerator where by combustion of coke deposited on the catalyst with air in a controlled manner. In order to maximise combustion rate and minimise the combustion temperature, combustion promoters are added, known by the persons in the art. The combustion promoters consist of platinum on alumina carriers. In case not enough coke is deposited during conversion of X or of C4-C7 olefins, additional fuel can be injected in the regenerator to provide heat to heat up more catalyst so that more heat can flow to the C4-C7 conversion zone. Examples of additional fuel are natural gas, LPG, heating oil or synthesis gas. In particular CO-rich synthesis gas is suitable. This CO-enriched synthesis gas is readily available in a methanol synthesis plant as for instance the purge stream of the methanol synthesis reactor loop.

Another source of hot catalyst is the XTO reactor zone as the conversion of X is strongly exothermic. The temperature of the catalyst, leaving the XTO zone should be at least higher than the temperature required at the outlet of the C4-C7 olefin cracking zone in order to obtain sufficient conversion. The conversion of C4-C7 olefins on hot catalyst conveying from the XTO zone is a kind of catalyst cooler for the XTO reaction zone.

BRIEF DESCRIPTION OF THE INVENTION

The present invention relates to a process to make light olefins, in a combined XTO-OC process, from an oxygen-containing, halogenide-containing or sulphur-containing organic feedstock comprising:
a) providing a catalyst comprising zeolitic molecular sieves containing at least 10 membered ring pore openings or larger in their microporous structure,
b) providing an XTO reaction zone, an OC reaction zone and a catalyst regeneration zone, said catalyst circulating in the three zones, such that at least a portion of the regenerated catalyst is passed to the OC reaction zone, at least a portion of the catalyst in the OC reaction zone is passed to the XTO reaction zone and at least a portion of the catalyst in the XTO reaction zone is passed to the regeneration zone;
c) contacting said oxygen-containing, halogenide-containing or sulphur-containing organic feedstock in the XTO reactor with the catalyst at conditions effective to convert at least a portion of the feedstock to form a XTO reactor effluent comprising light olefins and a heavy hydrocarbon fraction;
d) separating said light olefins from said heavy hydrocarbon fraction;
e) contacting said heavy hydrocarbon fraction in the OC reactor with the catalyst at conditions effective to convert at least a portion of said heavy hydrocarbon fraction to light olefins.

the XTO reaction zone can be made of one or more reactors.
the OC reaction zone can be made of one or more reactors.
the regeneration zone can be made of one or more reactors.
the XTO reaction zone and the OC reaction zone can be located in the same reactor.

The catalyst can be a mixture of two or more catalysts and optionally a binder.

It is an essential feature of the present invention that the same catalyst is used in the XTO and OC reaction zone.

It is desirable to have a substantially 100% conversion of the organic compound in the XTO reactor. This conversion rate is adjusted by optimization of contact time, reaction temperature and the frequency of regeneration of the catalyst.

In a specific embodiment the WHSV of X in the XTO reaction zone is from about 0.5 to about 4 h−1, advantageously from about 1 to about 2 and the WHSV in the OC reaction zone is from about 5 to about 12 h−1, advantageously from about 8 to about 12.

Advantageously the catalyst coming from the OC zone and flowing to the XTO section has to contain at least 0.1% carbon.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$. The $C_4^+$ fraction can also contain co-boiling X-containing compounds, like methanol and other oxygenates.

According to an embodiment the catalyst is a P-modified zeolite. These phosphorus modified molecular sieves of the present invention are prepared based on MFI, MOR, MEL, clinoptilolite or FER crystalline aluminosilicate molecular sieves having an initial Si/Al ratio advantageously between 4 and 500. These P-modified zeolites can also be obtained based on cheap crystalline alumosilicates with low Si/Al ratio (below 30). This provides a lower final catalyst cost.

The catalyst made of a P-modified zeolite can be the P-modified zeolite itself or it can be the P-modified zeolite formulated into a catalyst by combining with other materials that provide additional hardness or catalytic activity to the finished catalyst product.

According to a first embodiment said P-modified zeolite is made by a process comprising in that order:
  selecting a zeolite (advantageously with Si/Al ratio between 4 and 500) among $H^+$ or $NH_4^+$-form of MFI, MEL, FER, MOR, clinoptilolite;
  introducing P at conditions effective to introduce advantageously at least 0.05 wt % of P;
  separation of the solid from the liquid if any;
  an optional washing step or an optional drying step or an optional drying step followed by a washing step;
  a calcination step.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated. P can be introduced by any means or, by way of example, according to the recipe described in U.S. Pat. No. 3,911,041, U.S. Pat. No. 5,573,990 and U.S. Pat. No. 6,797,851. The separation of the liquid from the solid is advantageously made by filtering at a temperature between 0-90° C., centrifugation at a temperature between 0-90° C., evaporation or equivalent. Optionally, the zeolite can be dried after separation before washing. Advantageously said drying is made at a temperature between 40-600° C., advantageously for 1-10 h. This drying can be processed either in static conditions or in a gas flow. Air, nitrogen or any inert gases can be used. The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering. Final calcination step is performed advantageously at the temperature 400-700° C. either in static conditions or in a gas flow. Air, nitrogen or any inert gases can be used.

The catalyst made of a P-modified zeolite can be the P-modified zeolite itself or it can be the P-modified zeolite formulated into a catalyst by combining with other materials that provide additional hardness or catalytic activity to the finished catalyst product.

According to an embodiment of the invention the phosphorous modified zeolite is made by a process comprising in that order:
  selecting a zeolite (advantageously with Si/Al ratio between 4 and 500, from 4 to 30 in a specific embodiment) among $H^+$ or $NH_4^+$-form of MFI, MEL, FER, MOR, clinoptilolite;
  steaming at a temperature ranging from 400 to 870° C. for 0.01-200 h;
  leaching with an aqueous acid solution at conditions effective to remove a substantial part of Al from the zeolite;
  introducing P with an aqueous solution containing the source of P at conditions effective to introduce advantageously at least 0.05 wt % of P;
  separation of the solid from the liquid;
  an optional washing step or an optional drying step or an optional drying step followed by a washing step;
  a calcination step.

Optionally between the steaming step and the leaching step there is an intermediate step such as, by way of example, contact with silica powder and drying.

According to a second embodiment the catalyst of the combined XTO-OC process is a catalyst composite made by a process comprising the following steps:
  a). selecting a molecular sieve having pores of 10- or more-membered rings
  b). contacting the molecular sieve with a metal silicate comprising at least one alkaline earth metal, such that the composite comprises at least 0.1 wt % of silicate.

The molecular sieve is preferably brought into contact with the metal silicate by one of the following two methods:
  During the formulation step of the catalyst by mechanically blending the molecular sieve with the metal silicate forming a precursor to be used in the formulation step;
  Physical blending of the previously formulated molecular sieve and the previously formulated metal silicate in situ in the XTO and/or OC reaction medium.

The molecular sieve could be selected from the list of MFI, MOR, MEL, clinoptilolite, FER, FAU, MWW, BETA, ZSM-21, ZSM-22, ZSM-23, ZSM-42, ZSM-57, LTL, or a mixture of thereof. Preferably, the MFI is a ZSM-5 zeolite. More preferably, the molecular sieve is selected from the group of MFI, MOR, MEL, clinoptilolite, FER or a mixture thereof. In another embodiment, the molecular sieve is preferably obtained without direct addition of template. Said molecular sieve and/or said catalyst composite containing the molecular sieve and the metal silicate can be post-treated by calcinations, reductions or steaming. In the case of using zeolites as molecular sieve components, phosphorus can be introduced before, simultaneously or after blending with the metal silicate.

The composition of the catalyst composite comprises:
at least 10 wt % of a molecular sieve having pores of 10- or more-membered rings
at least one metal silicate comprising at least one alkaline earth metal, such that the catalyst composite comprises at least 0.1 wt % of silicate
optionally metal phosphates
optionally matrix material
optionally a binder.

According to a third embodiment, the catalyst of the combined XTO-OC process is an alkaline earth or rare earth metal —P-modified molecular sieve (M-P-modified molecular sieve) made by a process comprising the following steps:
  a). selecting at least one molecular sieve selected from one of:

a P-modified molecular sieve which contains at least 0.3 wt % of P
a molecular sieve which is modified with P prior to or during step
b) introducing at least 0.3 wt % of P
b). contacting said molecular sieve with an alkaline earth or rare earth metal-containing compound (M-containing compound) to introduce at least 0.05 wt % of the alkaline earth or rare earth metal M.

Optionally, the contact of the molecular sieve with the P-containing compound and the M-containing compound can be performed simultaneously.

The introduction of the alkaline earth or rare earth metal (M) is performed by bringing the molecular sieve in contact with a solution of one or more M-containing compounds. Said solution can contain a higher concentration of the alkaline earth or rare earth metal than that found in the final M-P-modified molecular sieve.

The modification of molecular sieves with phosphorous is known per se. This modification is carried out by treating molecular sieves with P-compounds in aqueous or non-aqueous media, by chemical vapor deposition of organic P-compounds or impregnation. The catalyst can be pre-formulated with binder or not. The preferred P-compounds used typically for this purpose can be selected from the group of phosphoric acid, $NH_4H_2PO_4$ or $(NH_4)_2HPO_4$.

The M-containing compound can be selected from organic compounds, salts, hydroxides and oxides. These compounds may also contain phosphorus. It is essential that these compounds are present in solubilized form, before bringing them into contact with the molecular sieve or by forming a solution when in contact with the molecular sieve.

The final molar ratio M/P in the M-P-molecular sieve is preferably less than 1.

The molecular sieve can be selected from the list of MFI, MOR, MEL, clinoptilolite, FER, FAU, MWW, BETA, MCM-41, ZSM-21, ZSM-22, ZSM-23, ZSM-42, ZSM-57, LTL or a mixture thereof. More preferably, the molecular sieve is selected from the group of MFI, MOR, MEL, clinoptilolite, FER or a mixture thereof. In the case of MFI, the molecular sieve is preferably a ZSM-5 zeolite. In another embodiment, the molecular sieve is preferably obtained without direct addition of template.

Preferably, the average pore size of the molecular sieve is at least 0.5 nm. Said molecular sieve before modification with M and P, can be calcined, steamed, ion-exchanged, treated with acid solution or it may undergo other treatments leading to dealumination. Dealumination of the molecular sieve can be performed simultaneously with the phosphorous modification.

DETAILED DESCRIPTION OF THE INVENTION

Figure 1:
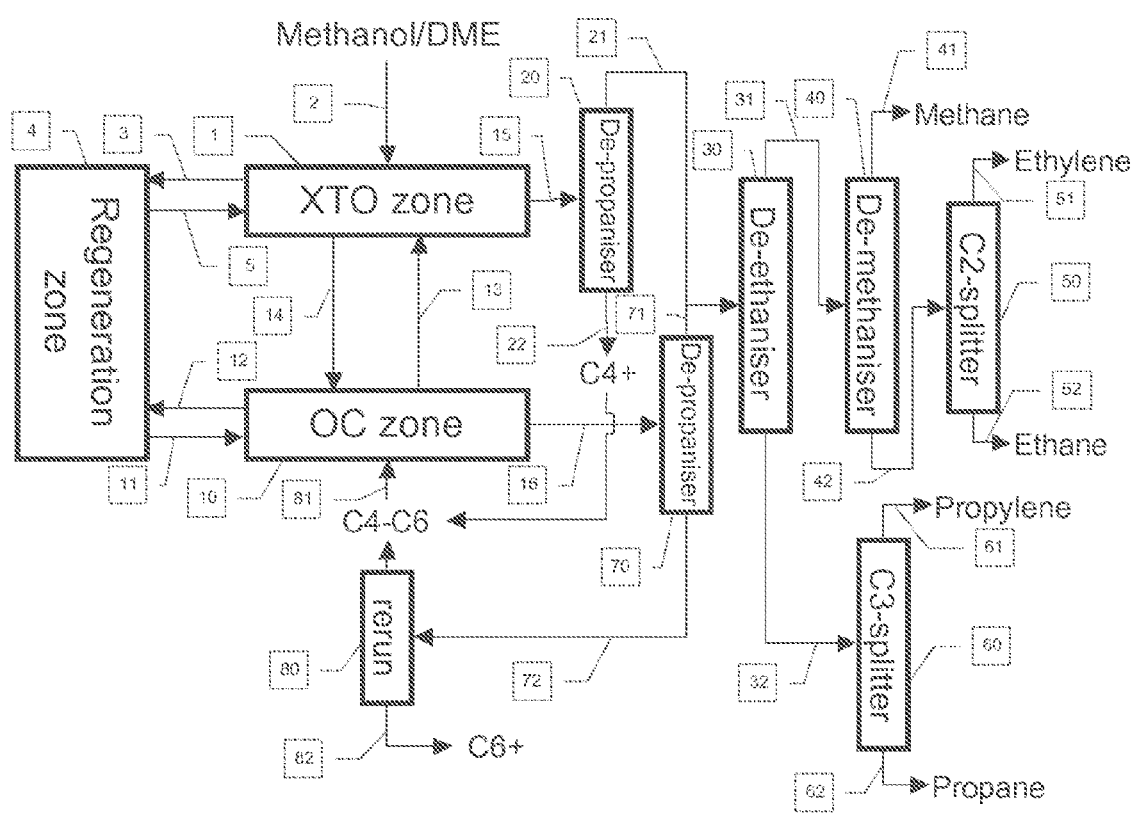
FIG. 1 depicts a general flow of catalyst between an OC reaction zone, XTO reaction zone and regeneration zone in accordance with one or more embodiments.

As regards the first embodiment of the invention, and the selected zeolite, advantageously it is a crystalline alumosilicate of the MFI family or the MEL family. An example of MFI silicates is ZSM-5. An example of an MEL zeolite is ZSM-11 which is known in the art. Other examples are described by the International Zeolite Association (*Atlas of Zeolite Structure Types,* 1987, Butterworths).

Crystalline silicates are microporous crystalline inorganic polymers based on a framework of $XO_4$ tetrahydra linked to each other by sharing of oxygen ions, where X may be trivalent (e.g. Al, B, ...) or tetravalent (e.g. Ge, Si, ...). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline alumosilicates are similar in size to many organic molecules of practical interest, they control the ingress and egress of reactants and products, resulting in particular selectivity in catalytic reactions. Crystalline alumosilicates with the MFI structure possess a bi-directional intersecting pore system with the following pore diameters: a straight channel along [010]: 0.53-0.56 nm and a sinusoidal channel along [100]: 0.51-0.55 nm. Crystalline alumosilicates with the MEL structure possess a bi-directional intersecting straight pore system with straight channels along [100] having pore diameters of 0.53-0.54 nm.

Advantageously the selected MFI, MEL, FER, MOR, clinoptilolite (or $H^+$ or $NH_4^+$-form MFI, MEL, FER, MOR, clinoptilolite) has an initial atomic ratio Si/Al of 100 or lower and from 4 to 30 in a specific embodiment. The conversion to the $H^+$ or $NH_4^+$-form is known per se and is described in U.S. Pat. No. 3,911,041 and U.S. Pat. No. 5,573,990.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

Advantageously the final P-content is at least 0.05 wt % and preferably between 0.3 and 7 w %. Advantageously at least 10% of Al, in respect to parent zeolite MFI, MEL, FER, MOR and clinoptilolite, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

The residual P-content is adjusted by P-concentration in the aqueous acid solution containing the source of P, drying conditions and a washing procedure if any. A drying step can be envisaged between filtering and washing steps.

The P-modified zeoilite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into spray-dried particles. The amount of P modified zeoilite which is contained in the final catalyst product ranges from 10 to 90 weight percent of the total catalyst, preferably 20 to 70 weight percent of the total catalyst.

As regards the second embodiment of the invention, The molecular sieves that can be used in the invention are preferably zeolites, for example crystalline silicates, more precisely aluminosilicates. Crystalline silicates are microporous crystalline inorganic polymers based on a framework of $XO_4$ tetrahydra linked to each other by sharing oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high surface area; uniform pores with one or more discrete sizes; ion exchangeability; good thermal stability; and ability to adsorb organic compounds. Since the pores of these crystalline aluminosilicates are similar in size to many organic molecules of practical interest, they control the ingress and egress of reactants and products, resulting in particular selectivity in catalytic reactions.

The selected molecular sieve can be made with the help of the seeding technique, but advantageously they are made without template. However, the seeds themselves may have been made with a template, which means in this case that the molecular sieve is made without direct addition of a template. It is preferred that the molecular sieve used in the invention is made without direct addition of template.

The molecular sieves selected for the purposes of this invention have pores of the size of 10 or more-membered rings. It can be envisaged to use molecular sieves, which have pores consisting of 10, 12 or more members.

The selected molecular sieve according to the present invention has an average pore size of at least 0.5, preferably from 0.5 to 10, more preferably from 0.5 to 5 and most preferably at least from 0.5 to 0.9 nm.

The selected molecular sieve has an initial atomic ratio Si/Al of at least 4 and not greater than 500. The Si/Al atomic ratio is measured by chemical analysis, for example using XRF and/or NMR. It includes only those Al that are part of the framework structure of the molecular sieve.

As regards to the selected molecular sieve, advantageously it is selected from the group of MFI, MOR, MEL, clinoptilolite, FER, FAU, MWW, BETA, ZSM-21, ZSM-22, ZSM-23, ZSM-42, ZSM-57, LTL, or mixtures thereof, according to the International Zeolite Association (*Atlas of Zeolite Structure Types*, 1987, Butterworths). Preferably it is selected from group of the MFI, MOR, MEL, clinoptilolite, FER or a mixture of thereof. More preferably, the MFI is a ZSM-5 zeolite. In another embodiment, the molecular sieve selected from the group of MFI, MOR, MEL, clinoptilolite, FER or a mixture of, is preferably obtained without direct addition of template. The molecular sieve may be used as synthesised to form the catalyst composite. Prior to formulation of the catalyst composite the molecular sieve may undergo further treatments including steaming, leaching (e.g. acid leaching), washing, drying, calcination, impregnation and ion exchanging steps. In addition or alternatively, these steps can also be carried out after formulation of the catalyst composite.

In a particular embodiment of the invention, the molecular sieve can be modified either prior to or after introduction of the metal silicate. Preferably, the molecular sieve has undergone some form of modification prior to the metal silicate introduction. By modification, it is meant herein that the molecular sieve may have undergone steaming, leaching (e.g. acid leaching), washing, drying, calcination, impregnation or some form of ion-exchange. This means that at least a portion of the cations originally comprised in the crystal structure can be replaced with a wide variety of other cations according to techniques well known in the art. The replacing cations can be hydrogen, ammonium or other metal cations, including mixtures of such cations.

The selected molecular sieve is then formulated into a catalyst composite to comprise at least 10% by weight of a molecular sieve as described herein and at least one metal silicate comprising at least one alkaline earth metal, such that the composite comprises at least 0.1% by weight of silicate.

At least one of the metal silicates comprised in the catalyst composite includes at least one alkaline earth metal, preferably Ca. Metal silicates are insoluble in water and alkaline earth metal ions, particularly calcium, are polyvalent and possess a large radius in the hydrated state. Thus, without wishing to be bound by theory, it is thought that the ion exchange reaction with the molecular sieve occurs very slowly, as the alkaline earth metal ion must lose many of its strongly coordinated water molecules in order to penetrate into the micropores of the molecular sieve structure. As a result, the alkaline earth metal ions expose only the acid sites located on the external surface of the molecular sieve, and thus increasing the selectivity of the catalyst.

Furthermore, without wishing to be bound by theory, it is thought that the presence of silicate anions further improve the catalytic properties of the catalyst composite. The silicate anions, for example, can supply silicon atoms to heal defects in the molecular sieve. This can thus lead to additional stabilisation of the catalyst under severe hydrothermal conditions. As a result the metal silicate acts as a catalyst promoter.

The metal silicate can comprise more than one alkaline earth metal selected from Ca, Mg, Sr and Ba.

The metal silicates may also comprise other metals selected from one or more of the following: Ga, Al, Ce, In, Cs, Sc, Sn, Li, Zn, Co, Mo, Mn, Ni, Fe, Cu, Cr, Ti and V. Preferably, the other metal is selected from one or more of Al, Mg, Ce, Co and Zn or mixtures thereof. These bi-, tri- or polymetal silicates can be synthesised according to any method known in the art. This can be for example by ion exchange in the solution or solid state (Labhsetwar et al., Reactivity of Solids, Vol. 7, Issue 3, 1989, 225-233).

The silicate anion can be present in any form in the solid metal silicate. Examples include $SiO_3^{2-}$, $SiO_4^{4-}$, $Si_2O_7^{6-}$, $Si_3O_{10}^{8-}$ and the like.

The preferred catalyst promoter is a calcium silicate with a very open and accessible pore structure. An even more preferred catalyst promoter comprises a synthetic crystalline hydrated calcium silicate having a chemical composition of $Ca_6Si_6O_{17}(OH)_2$ which corresponds to the known mineral xonotlite (having a molecular formula $6CaO.6SiO_2.H_2O$). Generally, a synthetic hydrated calcium silicate is synthesised hydrothermally under autogeneous pressure. A particularly preferred synthetic hydrated calcium silicate is available in commerce from the company Promat of Ratingen in Germany under the trade name Promaxon.

In order to demonstrate the thermal stability of xonotlite, and therefore the applicability of xonotlite as a catalyst promoter in MTO and OC, commercial xonotlite sold under the trade name Promaxon D was calcined in ambient air at a relative humidity of about 50% at 650° C. for a period of 24 hours. The initial xonotlite had a crystalline phase $Ca_6Si_6O_{17}(OH)_2$ with a BET surface area of 51 $m^2$/gram and a pore volume (of less than 100 nanometers) of 0.35 ml/gram. After calcination at 650° C., the carrier retained its crystallinity, which corresponds to that of xonotlite. Thus after a 24 hour calcination at 650° C., the crystalline phase still comprised xonotlite ($Ca_6Si_6O_{17}(OH)_2$) with a BET surface area of 47.4 $m^2$/gram and a pore volume (less than 100 nanometers) of 0.30 ml/gram.

Other examples of metal silicates comprising alkaline earth metals include $CaAl_2Si_2O_8$, $Ca_2Al_2SiO_7$, $CaMg(Si_2O_6)_x$, as well as mixtures thereof.

Before mixing with the molecular sieve said metal silicate compounds may be modified by calcination, steaming, ion-exchange, impregnation, or phosphatation. Said metal silicates may be an individual compound or may be a part of mixed compounds.

The metal silicate can be brought into contact with the molecular sieve by a simultaneous formulation step of a blend of the metal silicate with the molecular sieve or in situ blending of separately formulated materials in the reaction medium prior to the XTO or OC process. Said contact can be realised by mechanically blending of the molecular sieve with the alkaline earth metal-comprising metal silicate. This can be carried out via any known blending method. Blending can last for a period of time starting from 1 minute up to 24 hours, preferably from 1 min to 10 hours. If not carried out in the XTO or OC reactor in situ, it can be carried out in a batchwise mixer or in a continuous process, such as in an extruder e.g. a single or twin screw extruder at a temperature of from 20 to 300° C. under vacuum or elevated pressure. Said contact may be performed in an aqueous or non-aqueous medium. Prior to the formulation step, other compounds that aid the formulation may be added, like thickening agents or polyelectrolytes that improve the cohesion, dispersion and flow properties of the precursor. In case of oil-drop or spray-drying a rather liquid (high water content) is prepared. In another embodiment, the contact is carried out in the presence of phosphorus containing compounds. In a particular embodiment, the contact is carried out in the aqueous medium at pH lower than 5, more preferably lower than 3.

Either prior to, after or simultaneously with the formulation step to form the composite, other components may be optionally blended with the molecular sieve. In a particular embodiment, the molecular sieve can be combined with other materials that provide additional hardness or catalytic activity to the finished catalyst product. Materials, which can be blended with the molecular sieve, can be various inert or catalytically active matrix materials and/or various binder materials. Such materials include clays, silica and/or metal oxides such as alumina. The latter is either naturally occurring or in the form of gelatinous precipitates or gels including mixtures of silica and metal oxides. In an embodiment, some binder materials can also serve as diluents in order to control the rate of conversion from feed to products and consequently improve selectivity. According to one embodiment, the binders also improve the attrition of the catalyst under industrial operating conditions.

Naturally occurring clays, which can be used as binder, are for example clays from the kaolin family or montmorillonite family. Such clays can be used in the raw state as mined or they can be subjected to various treatments before use, such as calcination, acid treatment or chemical modification.

In addition to the foregoing, other materials which can be included in the catalyst composite of the invention include various forms of metals, phosphates (for instance metal phosphates, wherein the metal is chosen from one or more of Ca, Ga, Al, Ca, Ce, In, Cs, Sr, Mg, Ba, Sc, Sn, Li, Zn, Co, Mo, Mn, Ni, Fe, Cu, Cr, Ti and V), alumina or alumina sol, titania, zirconia, quartz, silica or silica sol, and mixtures thereof. Examples of possible phospates include amorphous calcium phosphate monocalcium phosphate, dicalcium phosphate, dicalcium phosphate dehydrate, α- or β-tricalcium phosphate, octacalcium phosphate, hydroxyapatite etc.

Examples of possibly binary oxide binder compositions include, silica-alumina, silica magnesia, silica-zirconia, silica-thoria, silica-beryllia, silica-titania, calcium-alumina. Examples of ternary binder compositions include for instance calcium-silica-alumina or silica-alumina-zirconia.

These components are effective in increasing the density of the catalyst and increasing the strength of the formulated catalyst. The catalyst usable in fluidised bed reactors has substantially spherical shape, formed typically by spray-drying. Generally, the size of the catalyst particles can vary from about 20 to 500 μm, more preferable from 30 to 100 μm The crystal size of the molecular sieve contained in the catalyst composite, is preferably less than about 10 μm, more preferably less than about 5 μm and most preferably less than about 2 μm. The amount of molecular sieve, which is contained in the final catalyst composite ranges from 10 to 90% by weight of the total catalyst composite, preferably 20 to 70% by weight.

According to another embodiment, non-modified molecular sieves were first formulated with a binder and matrix materials and then modified with phosphorous and alkaline earth metal silicates.

According to a further particular embodiment, molecular sieves were optionally dealuminated and then modified with phosphorous during the formulation step. Introduction of the alkaline earth metal silicate can be performed during the formulation step or on the formulated solid.

According to a preferred embodiment, molecular sieves were first optionally dealuminated and modified with phosphorous and then formulated. Introduction of the metal is performed simultaneously with the phosphorous modification step and/or on the already formulated catalyst.

After formulation, the catalyst composite may undergo further treatments including further steaming, leaching, washing, drying, calcination, impregnations and ion exchanging steps. If the molecular sieve was not modified with phosphorus prior to the formulation step of the blend i.e. the step introducing the metal silicate to the molecular sieve, it may be carried out after such a step.

According to a specific feature of this second embodiment, the molecular sieve is a phosphorus-modified (P-modified) zeolite. Said phosphorus-modified (P-modified) zeolite has already described above.

As regards the third embodiment of the invention, the molecular sieves have already been described in the second embodiment. Prior to P-modification and/or to the alkaline earth or rare earth metal-modification (M-modification), the molecular sieve may undergo further treatments including steaming, leaching (e.g. acid leaching), washing, drying, calcination, impregnation and ion exchanging steps. In addition or alternatively, these steps can also be carried out during or after P-modification. By ion exchanging steps, it is meant herein that at least a portion of the cations originally comprised in the crystal structure are replaced with a wide variety of other cations according to techniques well known in the art. The replacing cations can be hydrogen, ammonium or other metal cations, including mixtures of such cations.

For the purposes of this invention, modification of the molecular sieve with P must be carried out prior to or during M-modification, if the selected molecular sieve is not already P-modified. Preferably, the P-modification is carried out via a dealuminating steaming step followed by a leaching step using any acidic solution containing a source of P, preferably a solution of phosphoric acid. Preferably, the P-modified molecular sieve comprises at least 0.3% of phosphorus by weight of the molecular sieve.

According to one embodiment of the invention, the molecular sieve can be modified with phosphorus according to the process comprising the following steps, in the order given:

steaming of the molecular sieve at a temperature ranging from 400 to 870° C. for 0.01-200 h;

leaching with an aqueous acid solution containing the source of P at conditions effective to remove a substantial part of Al from the molecular sieve and to introduce at least 0.3% of phosphorus by weight of the molecular sieve;

Further modification can then be carried out according to the following steps, in the order given:

separation of the solid from the liquid;

an optional washing step or an optional drying step or an optional drying step followed by a washing step;

a calcination step.

Preferably, separation, optional washing and drying steps and calcination are carried out after introduction of the M-containing compound to the molecular sieve. The metal M can be any alkaline earth or rare earth metal. Preferably the alkaline earth metal is Ca. However, it is also possible to use Mg, Sr and Ba. Possible rare earth metals include La and Ce.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.05 to 200 hours, more preferably from 0.05 to 50 hours. It is generally known by the persons in the art that steam treatment of molecular sieves results in aluminium that leaves the molecular sieve framework and resides as aluminiumoxides in and outside the pores of the molecular sieve. This transformation is known as dealumination of molecular sieves and this term will be used throughout the text.

The treatment of the steamed molecular sieve with an acid solution results in dissolution of the extra-framework aluminiumoxide. This transformation is known as leaching and this term will be used throughout the text. The leaching with an aqueous acid solution containing the source of phosphorus is advantageously made under reflux conditions, meaning boiling temperature of the solution.

Amount of said acid solution is advantageously between 2 and 10 liters per kg of molecular sieve. A typical leaching period is around 0.5 to 24 hours. Advantageously the aqueous acid solution containing the source of P in the leaching step has a pH of 3, advantageously 2, or lower. Advantageously said aqueous acid solution is a solution of phosphorus acids, a mixture of phosphorus acids and organic or inorganic acids or mixtures of salts of phosphorus acids and organic or inorganic acids. The phosphorus acids or the corresponding salts can be of the phosphate ($[PO_4]^{3-}$, being tribasic), phosphite ($[HPO_3]^{2-}$, being dibasic), or hypophosphite ($[H_2PO_2]^{1-}$, being monobasic), type. Of the phosphate type also di- or polyphosphates ($[P_nO_{3n+1}]^{(n+2)-}$) can be used. The other organic acids may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, sulfuric acid or a salt of such an acid (e.g. the sodium or ammonium salts) or a mixture of two or more of such acids or salts.

It has been found that phosphorus acid is very efficient in complexing the extra-framework aluminiumoxides and hence removing them from the molecular sieve solid material. Unexpectedly, a larger quantity of phosphorus than what could be expected from the typical pore volume of the molecular sieve and assuming that the pores of the molecular sieves are filled with the used phosphorus acid solution, stays in the solid molecular sieve material. Both factors i.e. dealumination and the retention of P, stabilise the lattice aluminium in the zeolitic lattice, thus avoiding further dealumination. This leads to a higher hydrothermal stability, tuning of the molecular sieve's properties and adjustment of acid properties, thereby increasing the molecular sieve's selectivity. The degree of dealumination can be adjusted by the steaming and leaching conditions.

Advantageously, the final P-content of the molecular sieve is at least 0.3 wt % and preferably between 0.3 and 7 w %. Advantageously at least 10% of Al have been extracted and removed from the molecular sieve by the leaching. The residual P-content is adjusted by the P-concentration in the leaching solution, separating conditions during the separation of the solid from the liquid and/or the optional washing procedure during which impregnation and/or adsorption can also take place. A drying step can be envisaged between the separation and/or washing steps.

The molecular sieve is then either separated from the washing solution or is dried without separation from the washing solution. Said separation is advantageously made by filtration. Then the molecular sieve is calcined, by way of example, at 400° C. for 2-10 hours.

M-modification of the molecular sieve is carried out either on an already P-modified molecular sieve or during/after the P-modification process. P-modification can be carried out as described above wherein the sieve is dealuminated by steaming, then leached with a P-containing acid solution. In this case, advantageously, treatment of the molecular sieve with the M-containing solution is performed after the leaching or washing step i.e. after the phosphorous compound has been added and P-modification has taken place and before the separation step. However, the introduction of M to the molecular sieve can also be envisaged:

during the leaching step,
before the washing step but after leaching and drying
on calcined molecular sieves that have been contacted with P
on molecular sieve that has not been leached to introduce P but has been contacted with P during the washing step Introduction of M on the molecular sieves can be performed either by impregnation or by adsorption from an aqueous solution of M-containing compounds.

The introduction of the M-containing compound can be done at temperatures ranging from ambient temperature up to the boiling point of the solution.

The concentration of the M-containing compound in the solution is at least 0.05-M, preferably between 0.05 and 1.0 M. The amount of the alkaline earth or rare earth metal (M) in the M-P-molecular sieves can vary from at least 0.05% by weight, preferably 0.05 to 7% by weight, most preferably from 0.1 to 4% by weight.

Prior to formulation of the catalyst composite the molecular sieve may undergo further treatments including steaming, leaching (e.g. acid leaching), washing, drying, calcination, impregnation and ion exchanging steps. In addition or alternatively, these steps can also be carried out after formulation of the catalyst composite.

The alkaline earth or rare earth metal M is preferably selected from one or more of: Mg, Ca, Sr, Ba, La, Ce. More preferably, M is an alkaline earth metal. Most preferably, M is Ca. Particularly in the case of P-modification via steaming and leaching, M can be a rare earth metal such as La and Ce.

The M-containing compound is preferably in the form of an organic compound, a salt, hydroxide or oxide. The compound is preferably in a solubilized form when bringing it into contact with the molecular sieve. Alternatively, the solution of the M-containing compound can be formed after bringing the molecular sieve in contact with said compound.

Possible M-containing compounds include metal M compounds such as metal M sulphate, formate, nitrate, acetate, halides, oxyhalides, borates, carbonate, hydroxide, oxide and mixtures thereof. These can be for example, calcium sulphate, formate, nitrate, acetate, halides, oxyhalides, borates, carbonate, hydroxide, oxide and mixtures thereof.

The M-containing compound may also include other metals chosen from one or more of Mg, Sr, Ba, Ga, Al, Ce, In, Cs, Sc, Sn, Li, Zn, Co, Mo, Mn, Ni, Fe, Cu, Cr, Ti and V. The M-containing compounds may also additionally comprise phosphorus.

Those M-containing compounds, which are poorly water-soluble, can be dissolved to form a well-solubilized solution by heating and/or by modifying the pH of the solution by addition of phosphoric, acetic or nitric acid or corresponding ammonium salts of said acids. The concentration of the M-containing compound is at least 0.05 M.

The alkaline earth and rare earth metals M, in particular Ca, possess a large hydration sphere radius in the hydrated state. Thus, without wishing to be bound by theory, it is thought that the ion exchange reaction with the acid sites located on the inside of the micropore structures of the molecular sieve occurs very slowly. As a result, the chosen metal M exposes only the acid sites located on the external surface of the molecular sieve, and thus increasing the selectivity of the catalyst.

In the case of P-modified molecular sieves, M-modification leads to the formation of mixed M-Al-phosphates on the external surface. Taking into account that phosphorous is bound with the alkaline earth or rare earth metal M more strongly than with Al, this modification leads to stabilization of phosphorous on the external surface of the molecular sieve where the phosphorous is the most labile. However, it is essential, that all the M atoms located on the external surface are saturated with phosphorous. This can be guaranteed in the presence of an excess of phosphorous and by the presence of M in solution form, which is, for example, used to wash the excess phosphorous away preventing a plugging of the entrance to micropores.

Formulation into a catalyst composite can be carried out once the M-P-modified molecular sieve has been obtained i.e. other components may be optionally blended with the molecular sieve. (However, the M-P-modified molecular sieve can also be used as such as a catalyst.)

According to one embodiment, the prepared M-P-modified molecular sieve is co-formulated into a catalyst composite to comprise at least 10% by weight of the M-P-molecular sieve as described herein and at least 0.05% by weight of M and at least 0.3% by weight of phosphorous, both in relation to the weight of the molecular sieve.

In a particular embodiment, the molecular sieve can be combined with other materials that provide additional hardness or catalytic activity to the finished catalyst product. Materials, which can be blended with the molecular sieve, can be various inert or catalytically active matrix materials and/or various binder materials. Such materials include clays, silica and/or metal oxides such as alumina.

According to another embodiment, non-modified molecular sieve was first formulated with a binder and a matrix materials and then modified with phosphorous and metals.

According to particular embodiment, molecular sieves were optionally dealuminated and then modified with phosphorous during formulation step. Introduction of the metal can be performed during the formulation step or on the formulated solid.

According to preferred embodiment, molecular sieves was first optionally dealuminated and modified with phosphorous and then formulated. Introduction of the metal is performed simultaneously with modification with phosphorous step or/and on formulated catalyst.

The catalyst composite may also optionally comprise binder and/or matrix material and/or metal phosphate. Preferably, the amount of molecular sieve, which is contained in the final catalyst composite can range from 10 to 90% by weight of the total catalyst composite, more preferably from 20 to 70% by weight. The concentration of M in the formulated catalyst can be higher than the M concentration in the molecular sieve alone, because the binder or matrix material may also contain some M-compounds.

Naturally occurring clays, which can be used as binder, are for example clays from the kaolin family or montmorillonite family. Such clays can be used in the raw state as mined or they can be subjected to various treatments before use, such as calcination, acid treatment or chemical modification.

In addition to the foregoing, other materials which can be included in the catalyst composite of the invention include various forms of metals, phosphates (for instance metal phosphates, wherein the metal is chosen from one or more of Ca, Ga, Al, Ca, Ce, In, Cs, Sr, Mg, Ba, Sc, Sn, Li, Zn, Co, Mo, Mn, Ni, Fe, Cu, Cr, Ti and V), alumina or alumina sol, titania, zirconia, quartz, silica or silica sol, and mixtures thereof. Examples of possible phosphates include amorphous metal phosphates, and metal phosphates such as calcium phosphates e.g. monocalcium phosphate, dicalcium phosphate, dicalcium phosphate dehydrate, α- or β-tricalcium phosphate, octacalcium phosphate, hydroxyapatite etc. Examples of possibly binary binder compositions include, silica-alumina, silica magnesia, silica-zirconia, silica-thoria, silica-beryllia, silica-titania, calcium-alumina and calcium silicate. Examples of ternary binder compositions include for instance calcium-silica-alumina or silica-alumina-zirconia.

With regards to the XTO reaction zone, in this process a feedstock containing an oxygen-containing, halogenide-containing or sulphur-containing organic compound contacts the above described catalyst in a reaction zone of a reactor at conditions effective to produce light olefins, particularly ethylene and propylene. Typically, the oxygen-containing, halogenide-containing or sulphur-containing organic feedstock is contacted with the catalyst when the oxygen-containing, halogenide-containing or sulphur-containing organic compound is in vapour phase. Alternately, the process may be carried out in a liquid or a mixed vapour/liquid phase. In this process, converting oxygen-containing, halogenide-containing or sulphur-containing organic compounds, olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 600° C. is preferred.

The pressure also may vary over a wide range. Preferred pressures are in the range of about 5 kPa to about 5 MPa, with the most preferred range being of from about 50 kPa to about 0.5 MPa. The foregoing pressures refer to the partial pressure of the oxygen-containing, halogenide-containing, sulphur-containing organic compounds and/or mixtures thereof.

The process can be carried out in any system using a variety of fluidized bed reactors. It is particularly desirable to operate the reaction process at high space velocities. The process can be conducted in a single reaction zone or a number of reaction zones arranged in series or in parallel. After a certain time-on-stream the catalyst needs to be regenerated. This regeneration is carried out in the regeneration zone. The commercial scale reactor systems can be operated at a weight hourly space velocity (WHSV) of from 0.1 $hr^{-1}$ to 1000 $hr^{-1}$.

One or more inert diluents may be present in the feedstock of the XTO reaction zone, for example, in an amount of from 1 to 95 molar percent, based on the total number of moles of all feed and diluent components fed to the reaction zone. Typical diluents include, but are not necessarily limited to, helium, argon, nitrogen, carbon monoxide, carbon dioxide, hydrogen, water, paraffins, alkanes (especially methane, ethane, and propane), aromatic compounds, and mixtures thereof. The preferred diluents are water and nitrogen. Water can be injected in either liquid or vapour form.

The use of a diluents can provide two advantages. The first advantage is that it reduces the partial pressure of the X and hence will improve the selectivity for light olefins, mainly propylene. The result is that lower reaction temperatures can be used. Generally, the lower the partial pressure of X, the higher the light olefin selectivity. There exist an optimum for light olefin yield depending on the partial pressure, reaction temperature and catalyst properties.

The second advantage of using a diluents is that it can acts as a heat sink for the exothermic X conversion. So the higher the specific molar heat capacity, the more heat can be absorbed by the diluents. This second advantage might be less important in case of fluidised bed reactors as the latter are known to be excellent reactors to run at near homogeneous temperature throughout the catalyst bed. It is preferred that the diluents can be easily separated from the light olefins products, preferentially by simply phase separation. Hence a preferred diluents is water. Diluents can be added from 1 to 95 mole percent of the combined feed (X+diluents), preferably from 10 to 75 mole percent.

According to a specific embodiment essentially no water (or steam) is injected as diluent of the feedstock sent to the XTO reactor. However it means that the feedstock can contain the water already contained in the fresh oxygen-containing, halogenide-containing or sulphur-containing organic feedstock or the steam used to engage the proper flowing and purging of catalyst in fluidised bed reactors of the XTO reactor.

The oxygenate feedstock is any feedstock containing a molecule or any chemical having at least an oxygen atom and capable, in the presence of the above catalyst, to be converted to olefin products. The oxygenate feedstock comprises at least one organic compound which contains at least one oxygen atom, such as aliphatic alcohols, ethers, carbonyl compounds (aldehydes, ketones, carboxylic acids, carbonates, esters and the like). Representative oxygenates include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Representative oxygenates include lower straight chain or branched aliphatic alcohols, their unsaturated counterparts. Analogously to these oxygenates, compounds containing sulphur or halides may be used. Examples of suitable compounds include methyl mercaptan; dimethyl sulfide; ethyl mercaptan; di-ethyl sulfide; ethyl monochloride; methyl monochloride, methyl dichloride, n-alkyl halides, n-alkyl sulfides having n-alkyl groups of comprising the range of from about 1 to about 10 carbon atoms; and mixtures thereof. Preferred oxygenate compounds are methanol, dimethyl ether, or a mixture thereof.

In XTO effluent among the olefins having 4 carbon atoms or more there are more then 50 weight % of butenes.

With regards to said effluent of the XTO process, "light olefins" means ethylene and propylene and the "heavy hydrocarbon fraction" is defined herein as the fraction containing hydrocarbons having a molecular weight greater than propane, which means hydrocarbons having 4 carbon atoms or more and written as $C_4^+$. The $C_4^+$ fraction can also contain other co-boiling X-containing compounds, like methanol and other oxygenates.

The heavy hydrocarbon fraction produced in the XTO reactor is converted in the OC reactor to produce additional amounts of ethylene and propylene.

As regards the OC reaction zone, various reaction pathways can occur on the catalyst. Under the process conditions, having an inlet temperature of around 400° to 600° C., preferably from 520° to 600° C., yet more preferably 540° to 580° C., and an olefin partial pressure of from 0.1 to 2 bars, most preferably around atmospheric pressure. Olefinic catalytic cracking may be understood to comprise a process yielding shorter molecules via bond breakage.

In the catalytic cracking process of the OC reactor, the process conditions are selected in order to provide high selectivity towards propylene or ethylene, as desired, a stable olefin conversion over time, and a stable olefinic product distribution in the effluent. Such objectives are favoured with a low pressure, a high inlet temperature and a short contact time, all of which process parameters are interrelated and provide an overall cumulative effect.

The process conditions are selected to disfavour hydrogen transfer reactions leading to the formation of paraffins, aromatics and coke precursors. The process operating conditions thus employ a high space velocity, a low pressure and a high reaction temperature. The LHSV ranges from 0.5 to 30 hr$^{-1}$, preferably from 1 to 30 hr$^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The heavy hydrocarbon fraction feedstock is preferably fed at a total inlet pressure sufficient to convey the feedstocks through the reactor. Said feedstock may be fed undiluted or diluted in an inert gas, e.g. nitrogen or steam. Preferably, the total absolute pressure in the second reactor ranges from 0.5 to 10 bars. The use of a low olefin partial pressure, for example atmospheric pressure, tends to lower the incidence of hydrogen transfer reactions in the cracking process, which in turn reduces the potential for coke formation, which tends to reduce catalyst stability. The cracking of the olefins is preferably performed at an inlet temperature of the feedstock of from 400° to 650° C., more preferably from 450° to 600° C., yet more preferably from 540° C. to 590° C.

The OC reactor zone is also a fluidized bed. An example of fluid bed reactor is one of the FCC type used for fluidized-bed catalytic cracking in the oil refinery. The heavy hydrocarbon fraction cracking process is endothermic; therefore, the reaction zone should be adapted to supply heat as necessary to maintain a suitable reaction temperature.

A part of the catalyst is continuously or intermittently withdrawn from the conversion reactor (XTO) and sent to the regeneration zone. After the regeneration, at least a portion of the regenerated catalyst is continuously or intermittently sent to the OC reaction zone. Regeneration is carried out by injecting an oxygen-containing stream over the catalyst at sufficient high temperature to burn the deposited coke on the catalyst.

The OC reactor effluent comprises methane, light olefins and hydrocarbons having 4 carbon atoms or more. Advantageously said OC reactor effluent is sent to a fractionator and the light olefins are recovered. Advantageously at least a part of the hydrocarbons having 4 carbon atoms or more are recycled at the inlet of the OC reactor, optionally mixed with the heavy hydrocarbon recovered from the effluent of the XTO reactor. Advantageously, before recycling said hydrocarbons having 4 carbon atoms or more at the inlet of the OC reactor, said hydrocarbons having 4 carbon atoms or more are sent to a second fractionator to purge the heavies. In a preferred embodiment the light olefins recovered from the effluent of the XTO reactor and the light olefins recovered from the fractionator following the OC reactor are treated in a common recovery section.

In another embodiment the OC reactor effluent and the XTO reactor effluent are mixed and sent to a fractionator, or sent to the same fractionator, and the light olefins are recovered. At least a portion of the hydrocarbons having 4 carbon atoms or more are recycled at the inlet of the OC reactor. Advantageously, before recycling said hydrocarbons having 4 carbon atoms or more at the inlet of the OC reactor, said hydrocarbons having 4 carbon atoms or more are sent to a second fractionator to purge the heavies. The recovered light olefins are treated in a recovery section which is also called a common recovery section as in the above paragraph.

It is recommended, if the OC reactor feedstock contains dienes, to subject said feedstock to a selective hydrogenation process in order to remove the dienes.

Advantageously the paraffin's content in the feed at the inlet of the OC reactor is at least 20% weight on carbon basis, preferably at least 30%, more preferably 40%. Advantageously the paraffin's content in the feed at the inlet of the OC reactor is not more than 80% weight.

As regards the reactors, e.g. the XTO, and the OC reactors, for certain chemical reactor applications, the fixed bed reactors can have major disadvantages. When the reaction is fast and highly exothermic or endothermic, hot or cold spots will form in the packed beds and deteriorate the reactor performance. Sintering, plugging, and fluid maldistribution can also occur much more readily in packed beds in particular when coke deposition is rather fast. Comparing to fixed beds, fluidized beds can provide significant advantages when reactions are in particular highly exothermic or endothermic. Once the solids in the bed are fluidized, the solids inside the bed will behave just like liquid. The gas bubble size, shape, formation, rising velocity, and coalescence in the fluidized beds have quantitative similarity with those of gas bubbles in liquids.

The liquid like behavior of a fluidized bed thus allows the solids to be handled like a fluid, and continuous feeding and withdrawal therefore becomes possible. The rigorous mixing in a fluidized bed results in a uniform temperature even for highly exothermic or endothermic reactions and provides hence an smoother reactor control. The rigorous mixing also improves solids and fluid contacting, and it enhances heat and mass transfer.

There are many different variations of fluidized beds in practice, which are covered in available technical handbooks (e.g. Handbook of fluidization and fluid-particle system, Taylor&Francis Group LLC, 2003). The fluidization phenomena of gas-solids systems depend very much on the types of powders employed. There are several classifications, all based on the original work by Geldart. Many catalysts, used in fluidized bed systems are Group A particles, characterized by dense phase expansion after minimum fluidization and before the beginning of bubbling. Gas bubbles appear at the minimum bubbling velocity.

Fluidization regimes can be classified into two broad categories—particulate (smooth) and aggregative (bubbling). In particulate fluidization, the solid particles usually disperse relatively uniformly in the fluidizing medium with no readily identifiable bubbles. Thus the particulate fluidization sometimes is also called homogeneous fluidization. In the heterogeneous or aggregative fluidization, voids (bubbles) containing no solids are usually formed and are observed in a bubbling fluidized bed or in a slugging bed. For gas-solid systems, there are several distinguishable regimes of fluidization: fixed bed, particulate fluidization, bubbling fluidization, slugging fluidization, and turbulent fluidization for each of them criteria are available. When the operating velocity is higher than the transport velocity such that recycle of entrained particles is necessary to maintain a bed, additional fluidizing regimes are possible.

Particulate regime: $U_{mf} \leq U < U_{mb}$

For Group A powders, the fixed bed will expand homogeneously (particulate fluidization) above the minimum fluidization velocity ($U_{mf}$) and no bubbles will be observed as long as the velocity remains below the minimum bubbling velocity ($U_{mb}$).

Bubbling regime: $U_{mb} \leq U < U_{ms}$

The bubbles appear when the gas velocity is increased beyond the minimum bubbling velocity ($U_{mb}$). Gas bubbles form above distributor, coalesce and grow. The bubbling regime is characterized by the coexistence of a bubble phase and a dense/emulsion phase. The majority of the fluidizing gas is present in the form of bubbles, and as a result, the gas velocity through the dense phase is very low.

Slugging regime: $U_{ms} \leq U < U_c$

With large height-to-diameter bed ratios, the bed provides enough time for bubbles to coalesce into bigger ones. When the bubbles grow to approximately the size of the bed cross-section, the bed enters the slugging regime with periodic passing of large bubbles and regular large fluctuation of bed pressure drop. The velocity $U_c$ corresponds to the bed operating conditions where the slugs reach their maximum diameter and the amplitude of pressure fluctuation is highest.

Transition to Turbulent regime: $U_c \leq U < U_k$

When the gas velocity is continuously increased beyond this velocity $U_c$, large bubbles start to break up into smaller bubbles with smaller pressure fluctuation. This velocity is denoted as $U_k$, and characterizes the transition from the bubbling regime to the turbulent regime.

Turbulent regime: $U_k \leq U < U_{tr}$

Up to the transport velocity ($U_{tr}$) the bed is in turbulent regime. Bubbles or voids are still present, although they are less distinguishable in the dense suspension. In this regime, interactions between gas voids and the dense/emulsion phase are vigorous and provide an effective gas-solid contact.

Fast fluidized regime: $U > U_{tr}$

Beyond the transport velocity ($U_{tr}$), particles start to be entrained and continuous operation is no more possible without replacement or recycling of entrained and carried-over particles. Fast fluidized beds are typically characterized by a dense phase region at bottom, close to the distributor coexisting with a dilute phase region on top. The particle velocity increases with elevation in the bed and hence the bed density decreases.

Pneumatic conveying: $U >> U_{tr}$

All particles fed to the bottom of the fluidized bed are transported out in dilute phase with concentration varying along the bed height. A typical example is the riser fluidized bed used in FCC applications. Risers are vertical pipes with a high height-to-diameter ratio (>10) and the ideal riser approaches plug flow conditions such that both the catalyst as the fluid phase travels through the riser with minimum backmixing. Often, minimising backmixing of the fluid phase is essential for maximizing selectivity in chemical conversions.

In transport fluidized bed reactors (fast fluidized or pneumatic conveying) core-annulus flow can occur in which a high-velocity, dilute core is surrounded by a denser, slower-moving annulus. At low circulating mass fluxes, the solids in the annulus are flowing downward at the wall. At high circulating mass fluxes, the solids in the annulus flow up along the wall. This non-uniform flow phenomena will result in inefficient gas-solid contact and non-optimum catalyst performance and significant gas and solids backmixing will occur, especially when there is downflow in the wall region. For a fast fluidization, internals can be used to redistribute the axial and radial gas-solid flow structure, that is, to improve the uniformity of gas-solid flow structure in space and hence promote radial gas-solid exchange. The transport fluidized reactors required recirculation of catalyst particles back to the bottom of the reactor. This provides the possibility to control the catalyst density in the fluidized bed by recirculating more or less catalyst.

At the bottom of the fluidized bed, the feed fluid is homogenously distributed across the cross-section of the reactor vessel. At the end of the reaction zone, the reaction vapors are separated from the entrained catalyst by means of deflectors, disengagement zone and cyclones. The catalyst is collected, stripped from remaining hydrocarbons and can via standpipes and valves send back to the bottom of the fluidized bed zone.

For the exothermic XTO reaction, it is preferred to have an homogeneous temperature across (radial and axial) the catalyst bed in order to avoid hot spots and proper control of the catalytic reaction. This can be accomplished by fast recirculation and eventually backmixing of catalyst within the reactor vessel. Ways to control the average reaction temperature are by introducing the feed at a temperature lower than the average bed temperature and/or by removing heat from the catalyst bed by means of heat exchange. This heat exchange can be accomplished by internal heat exchange tubes through which a cooling medium flows and takes heat out of the reactor vessel or by external heat exchange by flowing the hot catalyst, collected from the top of the reactor, around heat exchanger tubes and recirculating the cooled catalyst back into the reactor vessel.

For the endothermic OC reaction, an homogeneous temperature across the catalyst bed is not always preferred as it would require significant overheating of the feed in order to provide the required reaction heat while the catalytic conversion rate would be lower due to the homogeneous lower temperature of the catalyst bed. A more plug-flow like reactor vessel allows operating the catalyst at a higher average temperature and by applying a high catalyst circulation rate allows introducing the required reaction heat by entrained hot catalyst. This hot catalyst can come from a regeneration section where the coke is burned and hence the catalyst absorbs the combustion heat or from the XTO reaction section where the catalyst absorbs the reaction heat from the exothermic XTO reaction. During the OC endothermic reaction the catalyst looses heat and the colder catalyst can be sent back to the MTO zone where again heat is absorbed form the MTO reaction.

As regards the catalyst regeneration, the combined XTO/OC reactor system has also a regenerator with primary objective to remove coke depositions on the catalyst by combustion with oxygen. Regenerators are mostly turbulent or fast fluidized bed systems. Typically, regenerator comprises a dens catalyst bed at the bottom of the vessel and a more dilute bed near the top of the vessel. Afterburning is the phenomenon when CO reacts with remaining oxygen in the dilute phase or in the freeboard of the vessel. The combustion of CO releases a lot of heat while little catalyst is present that gets overheated, resulting in irreversible deactivation. There are two types of regenerators, either operating in the partial combustion mode or in the total combustion mode. In partial combustion mode, less than stoichiometric amount of air is provided to the regenerator. Most of the carbon is reacted to carbon monoxide and only part is reacted to carbon dioxide. Ideally, all oxygen should be consumed and no oxygen should be present in the flue gas. The CO/CO2 ratio in the flue gas is typically in the range from 0.5 to 2.0. In the total combustion mode, excess air is provided to the regenerator. Ideally, all the carbon in the coke should be reacted to carbon dioxide, and no carbon monoxide should be present in the flue gas. The residual oxygen content in the flue gas is in the range from 1.0 to 3.0 percent on a dry basis. Partial combustion regenerators have several advantages over total combustion regenerators particularly when the catalyst is sensitive to high temperature and steam environment: (i) more coke can be burned at a given amount of air flow because it requires less than the stoichiometric amount of air and (ii) less combustion heat is released and hence moderate temperature control is possible which preserves better the catalytic activity in the presence of the produced steam from hydrogen combustion. A potential drawback of the partial combustion regenerator is higher remaining coke on regenerated catalyst. In case of total combustion regeneration, the remaining carbon on catalyst is low and catalyst activity restoration is higher. Potential drawback of total combustion regenerators includes higher heat release owing to total combustion reaction and hence more irreversible catalyst activity loss. Using two-stage regeneration can reduce catalyst deactivation. In the two-stage regeneration, the first stage is operated at a moderate temperature to burn off mainly the hydrogen, present in the coke, which has a higher reaction rate, beside some of the carbon. In the second stage, using excess air, the remaining carbon is burned at higher temperature to carbon dioxide and thanks to the absence of water vapor in the second stage regenerator, catalyst deactivation at high temperature can be minimized.

Afterburning can occur both in partial (breakthrough of oxygen out of the dense regenerator bed) and in full combustion mode (breakthrough of CO out of the dense regenerator bed), most of the time due to maldistribution of catalyst. Regenerators can be operated at low temperature (<650° C.), intermediate temperature (<700° C.) and high temperature (~730° C.). At low temperature full combustion is not feasible, but partial combustion can be operated stable. At intermediate temperature stable partial combustion is possible and full combustion is possible, provided combustion promoters are added. High temperature regeneration can operate stable both in partial as in full combustion mode. Combustion promoters or CO promoters assist to the complete conversion of CO into CO2 in the dense phase of the regenerator and prevents hence temperature excursion due to afterburning. These promoters can improve more uniform combustion of coke, particularly in cases of uneven distribution between coked catalyst and air. Combustion promoters are typically comprised of platinum (300-800 wppm) on alumina carrier and are added in order to reach 0.5-1.5 ppm of platinum in the catalyst inventory.

In case of XTO, no extra heat produced during regeneration is required for the XTO reaction as the latter itself is strongly exothermic. On the other hand extra heat can be used in the OC reaction zone, as the OC reaction is endothermic. If more heat is generated in the regenerator, in particular in full combustion mode, than what is required for the reaction, a catalyst cooler can be added to remove the excess heat. The catalyst cooler is a heat exchanger that produces steam while removing heat from the catalyst in the regenerator.

Optionally, in order to adjust the propylene to ethylene ratio of the whole process (XTO+OC), ethylene in whole or in part can be recycled over the OC reactor and advantageously converted into more propylene. This ethylene can either come from the separation section of the XTO reactor or from the separation section of the OC reactor or from both the separation section of the XTO reactor and the separation section of the OC reactor or even from the optional common recovery section.

Optionally, in order to adjust the propylene to ethylene ratio of the whole process (XTO+OC), ethylene in whole or in part can be recycled over the XTO reactor where it combines with the oxygen-containing, halogenide-containing or sulphur-containing organic feedstock to form more propylene. This ethylene can either come from the separation section of the XTO reactor or from the separation section of the OC reactor or from both the separation section of the XTO reactor and the separation section of the OC reactor or even from the optional common recovery section.

These ways of operation allow to respond with the same equipment and catalyst to market propylene to ethylene demand.

FIG. 1 illustrates the general flow of the catalyst between the OC reaction zone, the XTO reaction zone and the regeneration zone. DME means dimethylether. For simplicity of the drawing, the details of each specific equipment are not shown.

In the XTO zone (1) the X-containing compound coming via line (2) is converted into hydrocarbons that flow via line (15) to a depropaniser (20). The deactivated catalyst from the XTO zone goes via line (3) to the regenerator (4) where it is regenerated by means of combustion. Regenerated catalyst goes back via line (5) to the XTO zone. The OC zone (10) cracks the heavy olefins coming via line (81) into lighter olefins that go via line (16) to a depropaniser (70). The catalyst in the OC zone is sent via line (12) to the regenerator (4) for regeneration by means of combustion. The regenerated catalyst goes via line (11) back to the OC zone (10). Catalyst can also go via line (13) from the OC zone (10) to the XTO zone (1) and visa versa via line (14). The depropaniser (20) produces a light fraction that is sent via line (21) to a common deethaniser (30) and a heavy fraction that is sent via line (22) and line (81) to the OC zone (10). The depropaniser (70) produces a light fraction that is sent via line (71) to the common deethaniser (30) and a heavy fraction that is sent via line (72) to a rerun column (80). The rerun column (80) produces a C4-C6 fraction that is recycle via line (81) to the OC zone (10) and a C6+ fraction that is sent via line (82) to storage. The deethaniser (30) produces a fraction lighter than propylene that is sent via line (31) to a demethaniser (40) and a fraction containing mainly propylene and propane that is sent via line (32) to a C3-splitter (60). The C3-splitter (60) produces an overhead propylene product that is sent via line (61) to storage and a bottom propane product that is sent via line (62) to storage. The overhead (mainly methane and hydrogen) of the demethaniser (40) is sent via line (41) to a fuel gas system. The bottom product of the demethaniser (40) is sent via line (42) to a C2-splitter (50). The C2-splitter (50) produces an overhead ethylene product that is sent via line 51 to storage and a bottom ethane product that is sent via line (52) to storage.

Figure 2:
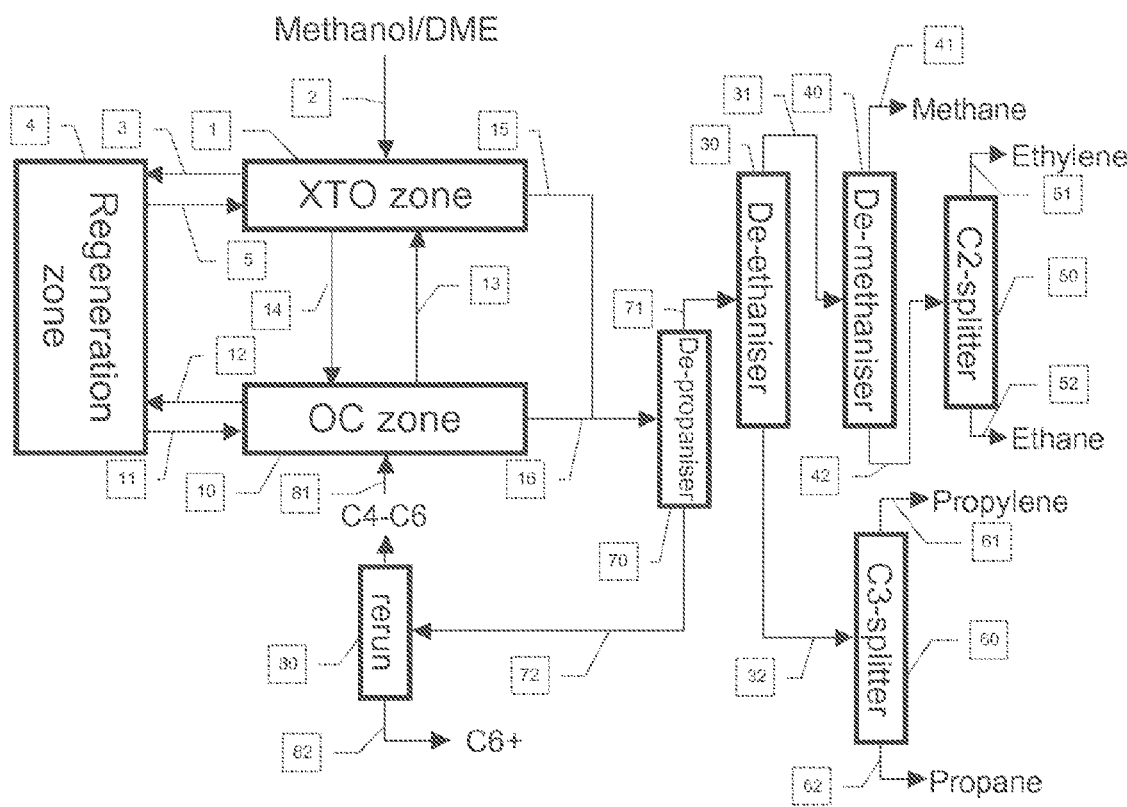
FIG. 2 depicts a separation system in accordance with one or more embodiments.

FIG. 2 illustrates a more specific embodiment of a separation section. The products of the XTO zone (1) via line (15) and of the OC zone (10) via line (16) flow to a common depropaniser (70). In this particular case, all heavy hydrocarbons produced as bottom product of the depropaniser (70) go via line (72) to the rerun column (80). The remaining is similar to the explanation of FIG. 1.

As regards the catalyst circulation, in a specific embodiment all the catalyst from the regenerator is sent to the OC reaction zone, then further sent to the XTO reaction zone and finally all the catalyst of the XTO reaction zone is sent to the regenerator (the regeneration zone) and to the OC reaction zone.

Figure 3:
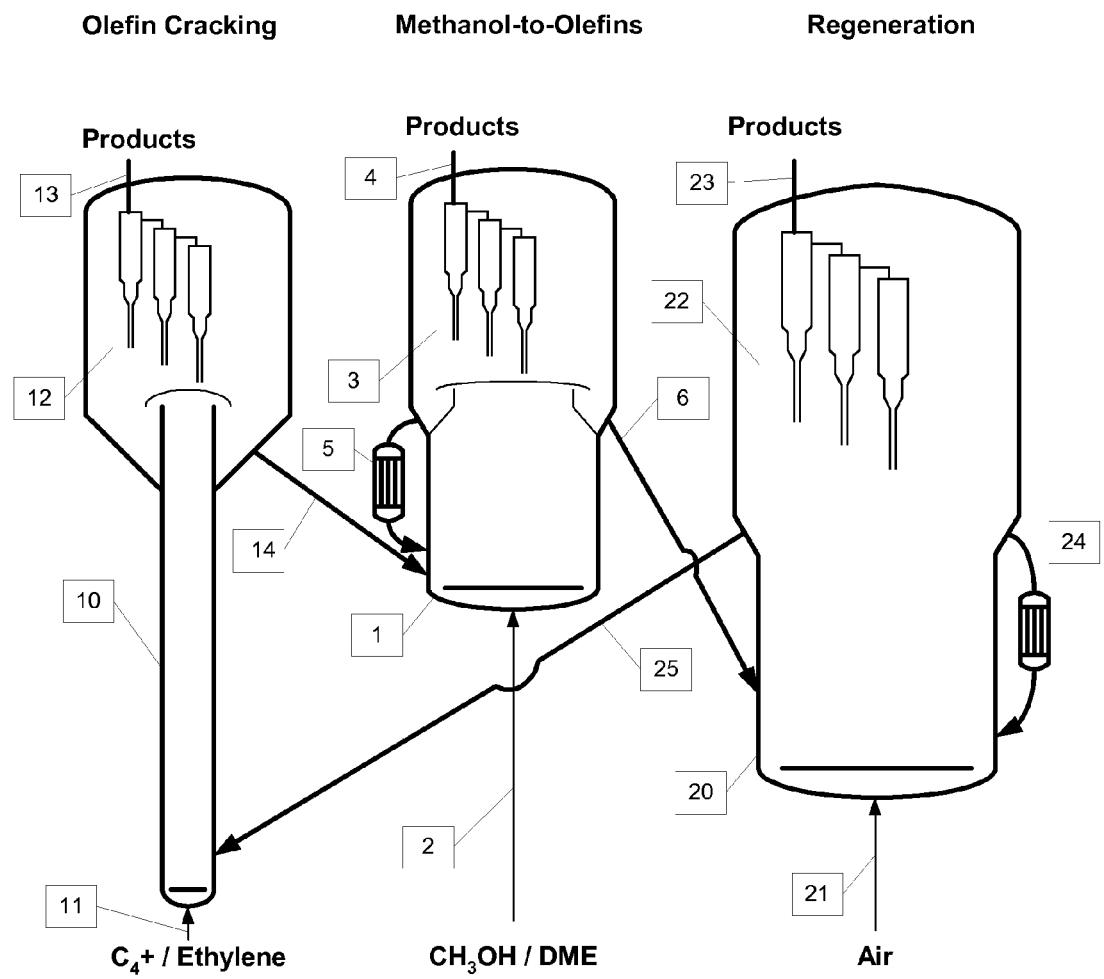
FIG. 3 depicts a flow of catalyst from a regeneration zone to an OC reaction, then to an XTO reaction zone, and then to the regeneration zone in accordance with one or more embodiments.

FIG. 3 illustrates in a specific embodiment the flow of the catalyst from the regeneration zone to the OC reaction zone, then to the XTO reaction zone and finally to the regeneration zone again. For sake of simplicity, details of the vessel internals are omitted from the drawings. Literature and persons skilled in the art easily understand the requirements of the vessel internals and auxiliary equipment. The X (here methanol/DME) is sent via line (2) into the fluidized bed XTO zone (1). In the top of the XTO zone (1) the products are separated from the catalyst in the disengagement/cyclone zone (3) and the products are sent via line 4 to a separation section. Optionally the heat of reaction produced during the XTO reaction can be extracted by means of a catalyst cooler (5). The XTO zone receives the catalyst via line (14) from the OC zone (10). The C4+ hydrocarbons and eventually ethylene is injected into the OC zone (10) via line (11). The catalyst, reactants and product travel to the disengagement/cyclone zone (12) where the products are separated from the catalyst. The products are sent to a separation section via line (13). The catalyst is withdrawn from the disengagement/cyclone zone (12) via line (14) to the XTO zone (1). The deactivated catalyst from the XTO zone (1) is withdrawn via line (6) to the regeneration zone (20). Air is injected via line (21) into the regeneration zone (20) where the coke deposits are burned. In the disengagement/cyclone zone (22), the combustion gases are separated from the catalyst and the combustion gases sent out via line (23). Optionally, as the combustion of coke deposits is very exothermic reaction and the temperature of the regeneration zone (20) need careful control, a catalyst cooler (24) can be installed through which the hot catalyst circulates in order to be cooled down which allows to control the temperature in the regeneration zone (20). The regenerated catalyst is sent via line (25) to the OC zone (10).

Figure 4:
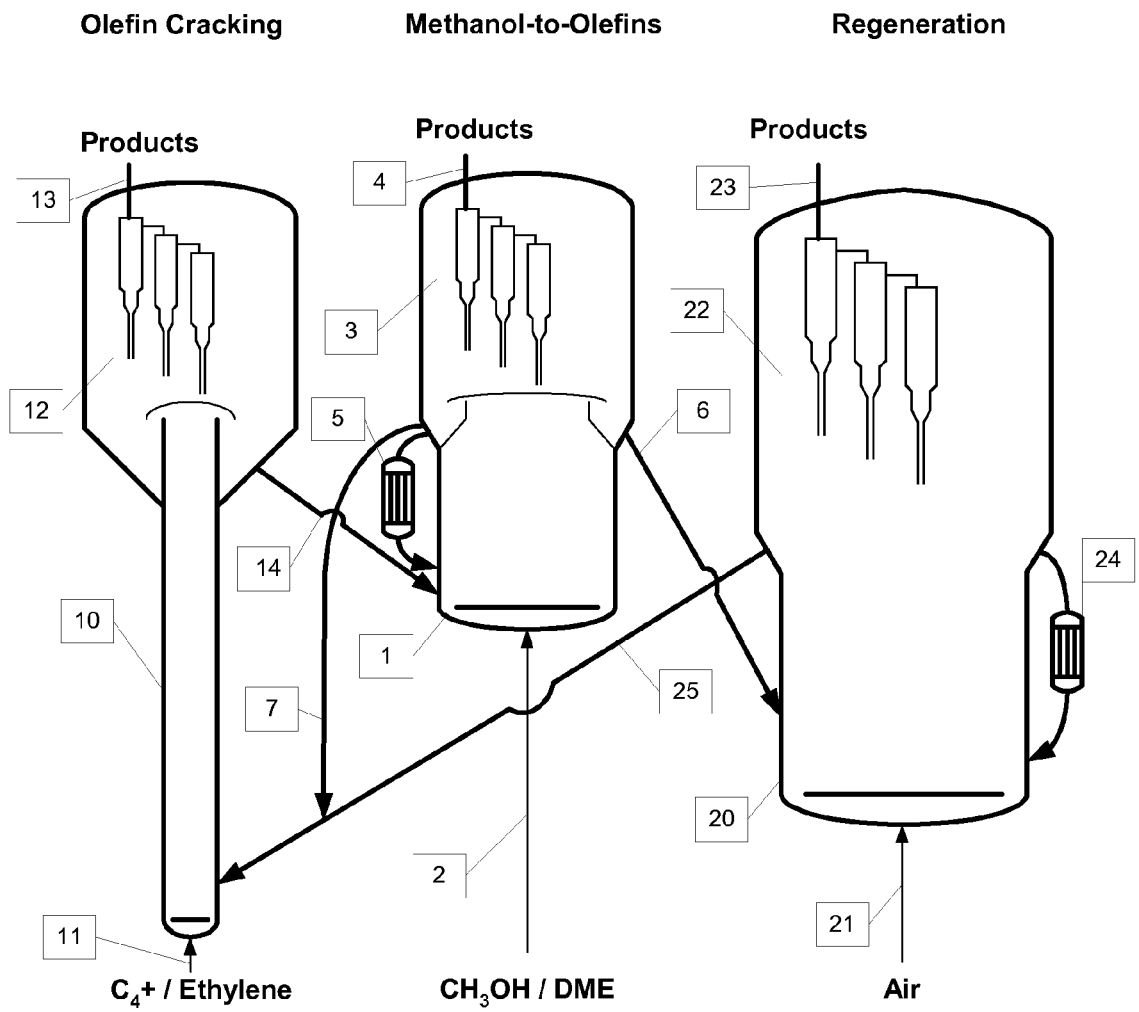
FIG. 4 depicts a flow of catalyst from a regeneration zone to an OC reaction, then to an XTO reaction zone, and then to the regeneration zone in accordance with one or more embodiments.

FIG. 4 illustrates a more specific embodiment of FIG. 3. At least of part of the catalyst present in the XTO zone (1) and separated from the products in the disengagement/cyclone zone (3) is sent via line (7) together with the fresh regenerated catalyst via line (25) to the OC zone (10). The remaining is similar to FIG. 3.

Figure 5:
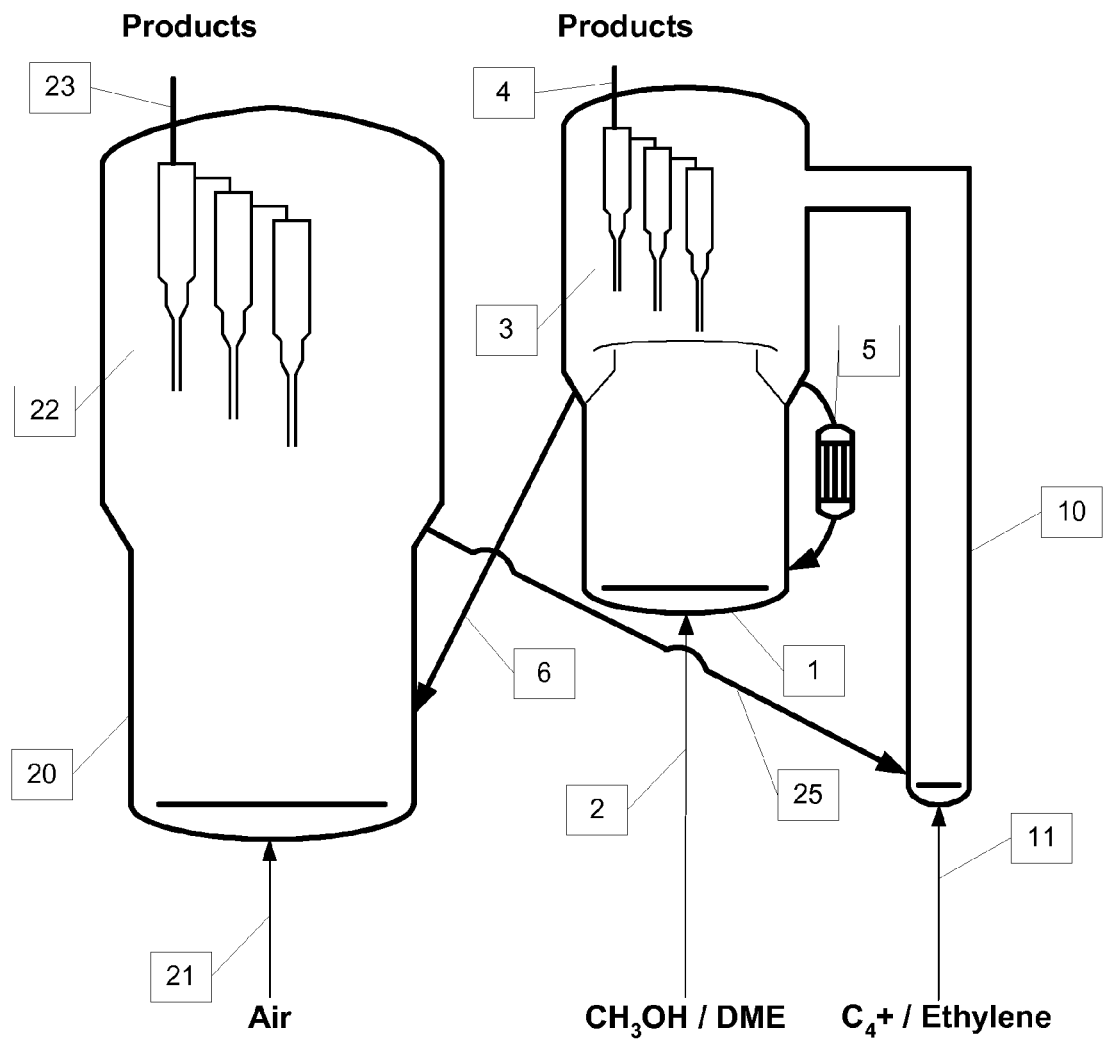
FIG. 5 depicts a common disengagement/cyclone zone in accordance with one or more embodiments.

FIG. 5 illustrates an embodiment where a common disengagement/cyclone zone for products and catalyst is used for the XTO and OC zone. The common disengagement/cyclone zone (3) is located at the top of the XTO zone (1). The end of the OC zone (10) is connected to the disengagement/cyclone zone (3) where the catalyst is separated from the products produced in the XTO (1) and OC (10) zones and sent via line 4 to a separation section. The regenerated catalyst is sent via line (25) from the regeneration zone (20) to the OC zone (10). The catalyst from the OC zone (10) is mixed with the catalyst entrained from the XTO zone (1) and separated from product in the common disengagement/cyclone zone (3) and flows back to the XTO zone via line (5) (which can consist optionally of a catalyst cooler as well). Part of this deactivated catalyst is sent via line (6) to the regeneration zone (20).

Figure 6:
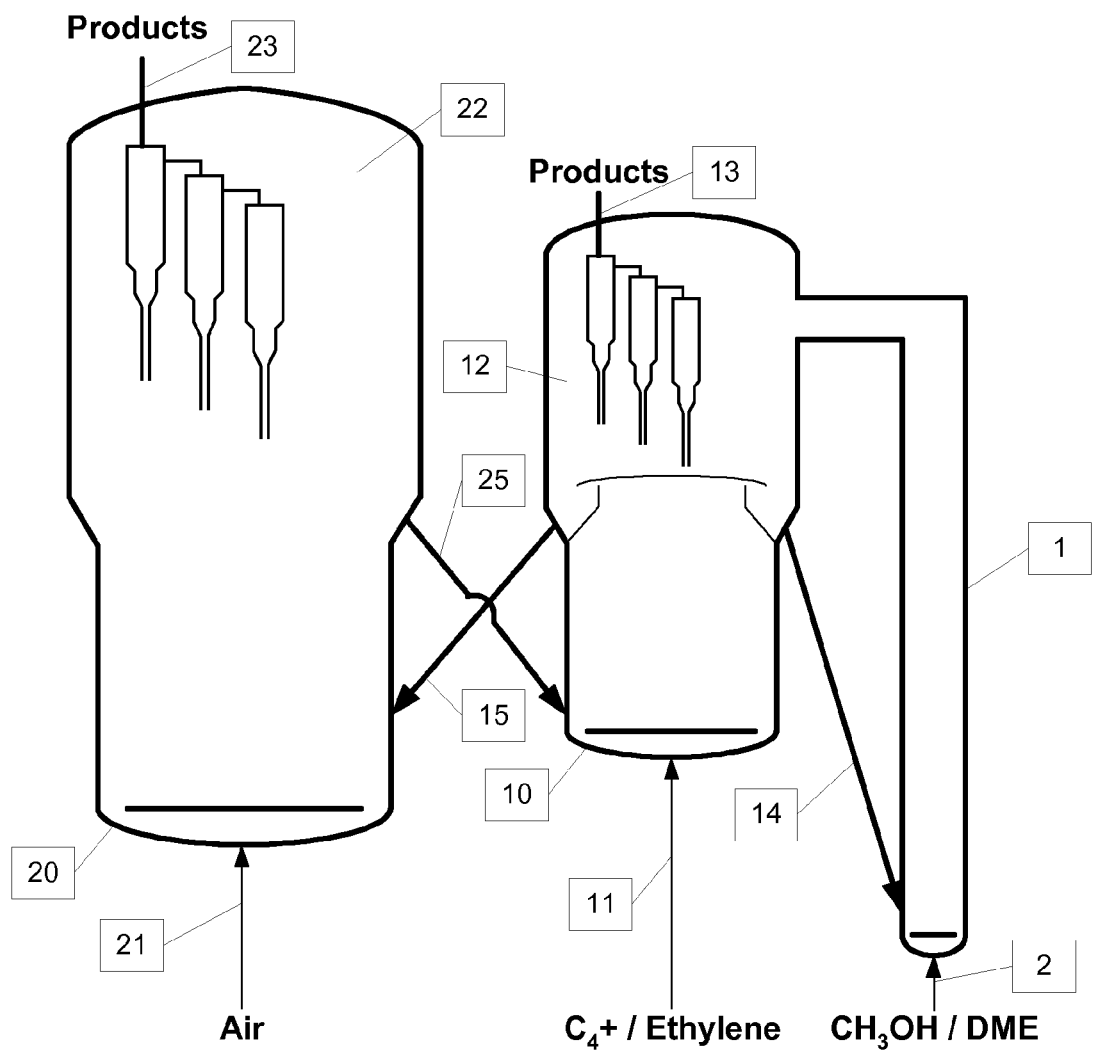
FIG. 6 depicts a common disengagement/cyclone zone in accordance with one or more embodiments.

FIG. 6 illustrates a more specific embodiment of FIG. 5 where the disengagement/cyclone zone is on the top of the OC zone (10). Regenerated catalyst is sent via line (25) from the regeneration zone (20) to the OC zone (10). At least a part of the catalyst in the OC zone (10) is sent via line 14 to the XTO zone (1). The catalyst and products from the XTO zone (1) flow to the common disengagement/cyclone zone (12) where they are mixed with the products and catalyst coming from the OC zone (10). Catalyst, separated in the disengagement/cyclone zone (12), is sent via line (15) to the regeneration zone (20). The mixed products are sent via line 13 to a separation section.

The method of making the olefin products from an oxygenate feedstock can include the additional step of making the oxygenate feedstock from hydrocarbons such as oil, coal, tar sand, shale, biomass, waste and natural gas. Methods for making oxygenate feedstocks are known in the art. These methods include fermentation to alcohol or ether, making synthesis gas, then converting the synthesis gas to alcohol or ether. Synthesis gas can be produced by known processes such as steam reforming, autothermal reforming and partial oxidation in case of gas feedstocks or by reforming or gasification using oxygen and steam in case of solid (coal, organic waste) or liquid feedstocks. Methanol, methylsulfide and methylhalides can be produced by oxidation of methane with the help of dioxygen, sulphur or halides in the corresponding oxygen-containing, halogenide-containing or sulphur-containing organic compound.

One skilled in the art will also appreciate that the olefin products made by the oxygenate-to-olefin conversion reaction using the molecular sieve of the present invention can be polymerized optionally with one or more comonomers to form polyolefins, particularly polyethylenes and polypropylenes. The present invention relates also to said polyethylenes and polypropylenes.

EXAMPLES

Example 1

A sample of zeolite ZSM-5 (Si/Al=13) in H-form synthesized without template was steamed at 550° C. for 6 h. Steamed solid was subjected to a contact with 3.14M solution of H3PO4 for 4 h under reflux condition (4.2 ml/1 g pf zeolite). Then the solid was separated from the liquid phase at room temperature by filtering from the solution. Obtained material was dried at 200° C. for 16 h. 10 g of the dried sample was subjected to a contact with 42 ml of water and 0.7 g of xonotlite (silicate of calcium) under stirring at room temperature for 1 h. Then 30 g of low sodium silica sol (2034DI Bindzil) and 2 g of kaolin were added to the solution. The resulted mixture was kept under stirring for one hour more at room temperature and dried. The dried powder was calcined at 700° C. for 2 h. The sample is hereinafter identified as sample A.

Example 2

(OC)

Catalyst tests were performed on sample A on 10 ml (6.3 g) of catalyst grains (35-45 meshes) loaded in a tubular reactor with internal diameter 11 mm. The feedstock which contains substantially non cyclic olefins C4 (62%) was subjected to catalytic cracking in the presence of catalyst in a fixed bed reactor at 575° C., WHSV=6.7 h$^{-1}$, P=1.5 bara.

The results of the average catalyst performance during the first 3 h are in table 1 hereunder. The values in table 1 are in weight percents on carbon basis.

Then the catalyst was cooled down under N$_2$ flow (5 Nl/h), unloaded and analysed for a carbon content by CHN method. The catalyst contained 0.2 wt % of carbon.

The unloaded spent sample of the catalyst containing 0.2 wt % of carbon is hereinafter identified as sample B (primarily used in OC reaction).

TABLE 1

|  | Feed | Effluent |
|---|---|---|
| C1 (Methane) | 0.0 | 0.3 |
| C2− (Ethylene) | 0.0 | 3.3 |
| C3 (Propane | 0.1 | 1.1 |
| C3− (Propylene) | 0.2 | 17.9 |
| C4 paraffin's | 33.9 | 34.4 |
| C4 olefins | 60.4 | 25.8 |
| C5+ | 5.3 | 42.1 |

TABLE 1-continued

|  | Feed | Effluent |
|---|---|---|
| Aromatics | 0.0 | 0.9 |
| Paraffins | 37.1 | 40.3 |
| Olefins | 62.3 | 58.1 |
| Aromatics | 0.0 | 0.9 |
| C3's purity | — | 94.9 |

Example 3

(MTO Reaction)

Catalyst tests were performed on 2 g (35-45 mesh particles) of catalyst with an essentially pure methanol feed, at 550° C. and at a pressure of 0.5 barg and WHSV=1.6 h$^{-1}$, in a fixed-bed, down flow stainless-steel reactor. Prior to catalytic run all catalysts were heated in flowing N$_2$ (5 Nl/h) up to the reaction temperature. Analysis of the products has been performed on-line by a gas chromatograph equipped with a capillary column. Catalytic performance of catalyst was measured at substantially full methanol conversion.

Regeneration of the spent catalyst was performed at 550° C. in N$_2$/Air flow (80/20) during at least 10 h. Then the catalyst was purged with N2 (5 Nl/h) for 1 h.

Fresh catalysts A, fresh catalyst A after 1 reaction/regeneration cycle, catalyst B (catalyst A primarily used in OC), and catalyst B regenerated after MTO reaction were evaluated in the MTO reaction.

Figure 7:
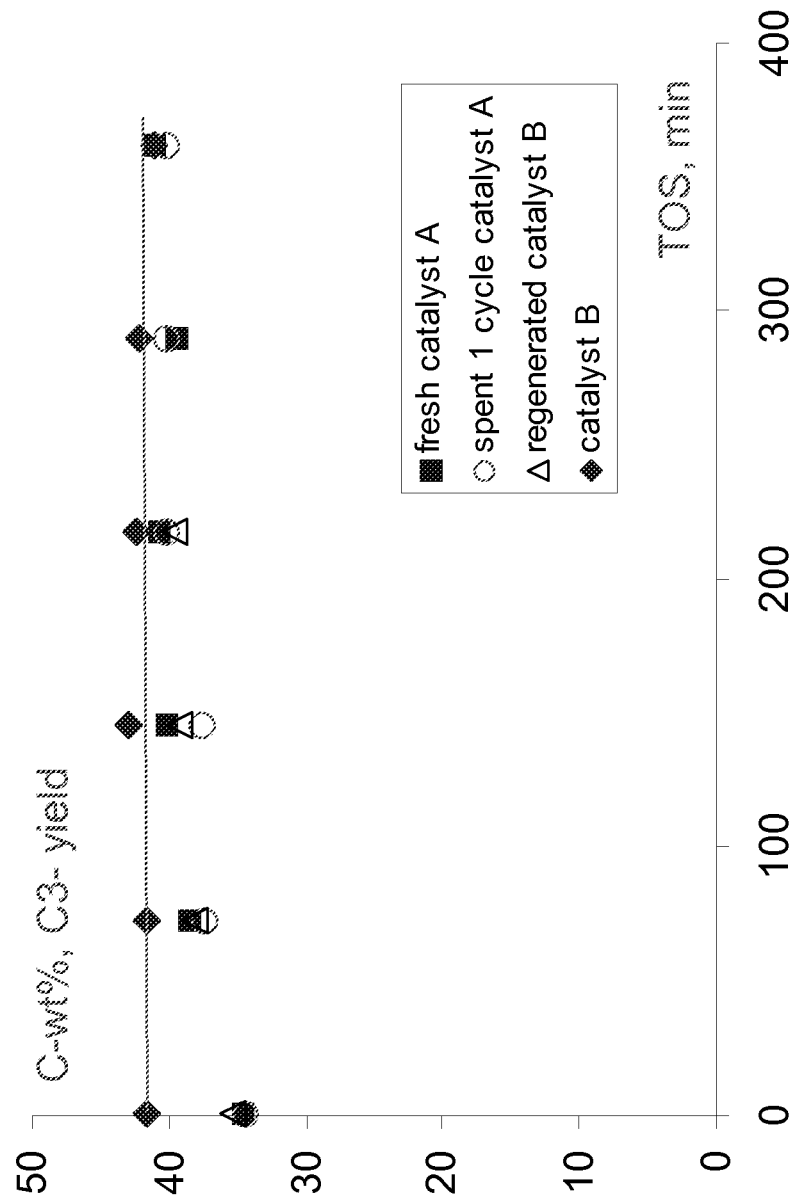
FIG. 7 depicts yield of propylene on carbon basis in accordance with one or more embodiments.

The yield of propylene on carbon basis are given in the FIG. 7.

The results given in the FIG. 7 illustrate a good catalyst performance of the P-ZSM-5 in MTO reaction and a beneficial effect of the primarily used (pre-coking) catalyst in OC reaction for use in MTO(sample B). Once the sample B after use in MTO is completely regenerated by coke combustion and used again for MTO, its performance becomes similar to that of fresh catalyst (sample A), illustrating the beneficial effect of primarily using fresh catalyst for OC reaction before using for MTO.

Example 4

A sample of zeolite ZSM-5 (Si/Al=13) in H-form synthesized without template was steamed at 550° C. for 6 h. 600 g of steamed sample was extruded with 37.5 g of xonotlite (silicate of calcium), and 330 g of silica sol (2034DI Bindzil) containing 34 wt % of SiO$_2$. The shaped sample was calcined at 400° C. for 6 h and subjected to a contact with 1M solution of H3PO4 for 4 h under reflux condition (4.2 ml/1 g pf zeolite). Then the solution containing the catalyst was cooled down and the solid was separated from the liquid phase at room temperature by filtering. Obtained material was dried at 110° C. for 16 h and calcined at 700° C. 2 h.

The sample is hereinafter identified as sample C.

Example 5

(OC Test)

Catalyst tests were performed on 10 ml (6.2 g) of catalyst C grains (35-45 meshes) loaded in a tubular reactor with internal diameter 11 mm. The feedstock which contains substantially non cyclic hydrocarbons C4 (63% olefins) was subjected to catalytic cracking at 575° C., WHSV=9.7 h$^{-1}$, P=1.5 bara.

Figure 8:
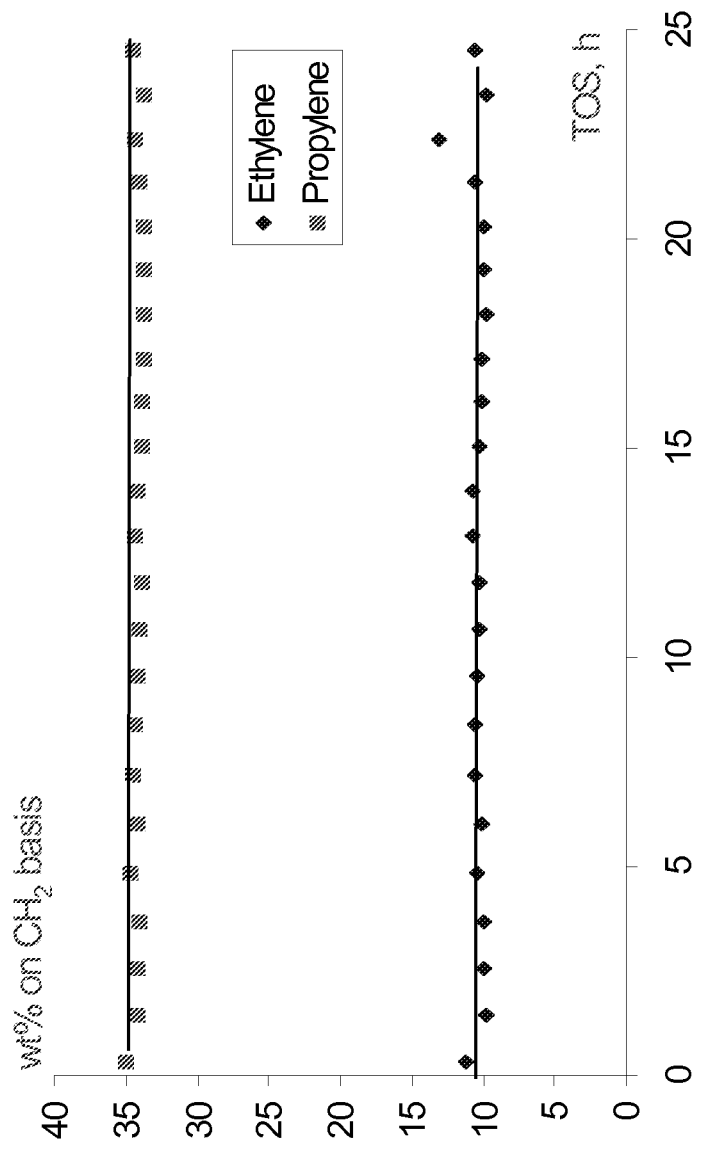
FIG. 8 depicts catalyst activity in an OC reaction zone in accordance with one or more embodiments.

The results of the average catalyst performance during the first 5 hours on stream are in table 2. FIG. 8 illustrates a stable activity of the catalyst C in OC reaction during 24 h. The values are in the weight percents on olefins (CH2) basis in the feed.

Example 6

Comparative (OC Test with Blended Feed, Recycling of 15% C4-C5)

Catalyst tests were performed on 10 ml (6.2 g) of catalyst C grains (35-45 meshes) loaded in a tubular reactor with internal diameter 11 mm. The feedstock which contains 85 wt % of MeOH and 10 wt % of non-cyclic C4 hydrocarbons (63% olefins) and 5 wt % of substantially non cyclic olefins C5 (59% olefins) was subjected to catalytic cracking in a fixed bed reactor at 550° C., WHSV=3.7 h$^{-1}$, P=1.5 bara.

The results of the average catalyst performance during the first 5 hours on stream are in table 2. The values are in the weight percents on olefins (CH2) basis.

Example 7

MTO Reaction

The MTO test was performed under the conditions given in the example 3 on the catalyst C.

The results representing the average catalyst activity 1-5 h TOS on olefins (CH2) basis dry basis are given in the table 2. The conditions are hereinafter identified as MTO. It is assumed that methanol contains 44 wt % of potential olefins (CH2).

The results given in the column "MTO+OC" represent the additive catalyst performance generated based on the results given in the example 7 and example 5 on fresh catalysts.

In ex 5+7 table 2 the results of said column are the sum of the columns on the left referred as CH2 from MeOH and CH2 from OC. The column CH2 from MeOH is 80.2% of the column ex 7 on the left and the column CH2 from OC is 19.8% of the column ex 6 on the left. This proves the advantage of two reaction zones over one reactor of ex 6.

Example 8

Comparative (OC Test with Blended Feed, Recycling of 30% C4-C5)

Catalyst tests were performed on 10 ml (6.2 g) of catalyst C grains (35-45 meshes) loaded in a tubular reactor with internal diameter 11 mm. The feedstock which contains 70 wt % of MeOH and 20 wt % of non-cyclic C4 hydrocarbons (63% olefins) and 10 wt % of substantially non cyclic olefins C5 (59% olefins) was subjected to catalytic cracking in a fixed bed reactor at 550° C., WHSV=3.7 h$^{-1}$, P=1.5 bara.

The results of the average catalyst performance during the first 5 hours on stream are in table 3. The values are in the weight percents on olefins (CH2) basis.

The results given in the tables 2-3 showed higher aromatic content and lower C3-/C2-ratio in case of recycling back in the MTO reactor the olefins C4-C5 providing higher olefins losses and potentially lower overall propylene yield in the process. In the contrary, performing the reaction in the two separated reaction zones allows optimizing each process and maximizes the yield of propylene.

TABLE 2

| | Example 7 MTO Yield on CH2 or olefins basis | Example 5 OC | 85 wt % MeOH 80.2 CH2-wt % (olefins wt %) CH2 from MeOH | 15 wt % C4-C5 19.8 CH2-wt % (olefins wt %) CH2 from OC | Example 5 + 7 MTO + OC Yield on CH2 or olefins basis | Example 6 (comparative) MeOH + C4-C5 |
|---|---|---|---|---|---|---|
| C2− | 12.2 | 10.3 | 9.8 | 2.0 | 11.8 | 13.1 |
| C3− | 40.6 | 34.6 | 32.6 | 6.8 | 39.4 | 37.7 |
| C2− + C3− | 52.8 | 44.8 | 42.3 | 8.9 | 51.2 | 50.8 |
| C3/C2 | 3.3 | 3.4 | 3.3 | 3.4 | 3.3 | 2.9 |
| Aromatics | 6.9 | 4.0 | 5.6 | 0.8 | 6.4 | 11.4 |
| Aromatic compounds | | | | | | |
| A6 | 0.38 | 0.4 | 0.3 | 0.08 | 0.3 | 0.7 |
| A7 | 1.70 | 1.5 | 1.4 | 0.29 | 1.7 | 3.2 |
| A8 | 3.26 | 1.5 | 2.6 | 0.30 | 2.9 | 5.2 |
| A9 | 1.40 | 0.6 | 1.1 | 0.11 | 1.2 | 1.9 |
| A10 | 0.15 | 0.1 | 0.1 | 0.02 | 0.1 | 0.3 |
| A11 | 0.01 | 0.1 | 0.0 | 0.01 | 0.0 | 0.1 |
| A9+ | 1.56 | 0.72 | 1.25 | 0.14 | 1.40 | 2.34 |

TABLE 3

| | Example 7 MTO Yield on CH2 or olefins basis | Example 5 OC | 70 wt % MeOH 65 CH2 wt % (olefins wt %) CH2 from MeOH | 30 wt % C4-C5 35 CH2 wt % (olefins wt %) CH2 from OC | Example 5 + 7 MTO + OC Yield on CH2 or olefins basis | Example 8 (comparative) MeOH + C4-C5 |
|---|---|---|---|---|---|---|
| C2− | 12.2 | 10.3 | 7.9 | 3.6 | 11.5 | 12.9 |
| C3− | 40.6 | 34.6 | 26.4 | 12.1 | 38.5 | 36.1 |
| C2− + C3− | 52.8 | 44.8 | 34.3 | 15.7 | 50.0 | 49.0 |
| C3/C2 | 3.3 | 3.4 | 3.3 | 3.4 | 3.3 | 2.8 |
| Aromatics | 6.9 | 4.0 | 4.5 | 1.4 | 5.9 | 10.6 |
| Aromatic compounds | | | | | | |
| A6 | 0.38 | 0.40 | 0.25 | 0.14 | 0.39 | 0.73 |
| A7 | 1.70 | 1.47 | 1.10 | 0.52 | 1.62 | 3.02 |
| A8 | 3.26 | 1.51 | 2.12 | 0.53 | 2.65 | 4.74 |
| A9 | 1.40 | 0.55 | 0.91 | 0.19 | 1.10 | 1.77 |
| A10 | 0.15 | 0.11 | 0.10 | 0.04 | 0.14 | 0.25 |
| A11 | 0.01 | 0.06 | 0.01 | 0.02 | 0.03 | 0.12 |
| A9+ | 1.56 | 0.72 | 1.02 | 0.25 | 1.27 | 2.14 |

The invention claimed is:

1. A process of making light olefins comprising:
   selecting a zeolite having an Si/Al ratio between 4 and 30 from an $H^+$ or $NH_4^+$ form of MFI, MEL, FER, MOR, or clinoptilolite;
   steaming the zeolite at a temperature ranging from 400 to 870° C. for 0.01-200 h;
   leaching the zeolite with an aqueous acid solution at conditions effective to remove at least 10% of Al from the zeolite;
   contacting the zeolite with an aqueous solution containing a source of P at conditions effective to introduce at least 0.05 wt % of P to form a solid zeolite in liquid;
   separating the solid zeolite from the liquid; and
   calcining the solid zeolite to form a P-modified zeolite;
   providing an oxygen-containing, halogenide-containing, or sulphur-containing organic feedstock;
   providing an Oxygenate to Olefin (XTO) reaction zone, an Olefin Cracking (OC) reaction zone and a catalyst regeneration zone, wherein one or more catalysts are in the XTO reaction zone and the same one or more catalysts are in the OC reaction zone and wherein each of the one or more catalysts is a zeolitic molecular sieves containing at least 10 membered rings pore opening in their microporous structure, wherein at least one of the catalysts comprises the P-modified zeolite,
   wherein the one or more catalysts circulate in the three zones, such that at least a portion of regenerated one or more catalysts is passed to the OC reaction zone, at least a portion of the one or more catalysts in the OC reaction zone is passed to the XTO reaction zone and at least a portion of the one or more catalysts in the XTO reaction zone is passed to the catalyst regeneration zone;
   contacting the oxygen-containing, halogenide-containing or sulphur-containing organic feedstock in the XTO reaction zone with the one or more catalysts at conditions effective to convert at least a portion of the feedstock to form an XTO reaction zone effluent comprising light olefins and a heavy hydrocarbon fraction;
   separating the light olefins from the heavy hydrocarbon fraction; and
   contacting the heavy hydrocarbon fraction in the OC reaction zone with the one or more catalysts at conditions effective to convert at least a portion of the heavy hydrocarbon fraction to light olefins.

2. The process of claim 1, further comprising washing, drying, or drying followed by washing the solid zeolite before calcining.

3. The process of claim 1, further comprising:
   contacting the zeolite with an alkaline earth or rare earth metal containing compound to introduce at least 0.05 wt % of an alkaline earth or rare earth metal (M).

4. The process of claim 1, wherein all of the one or more catalysts from the catalyst regeneration zone is sent to the OC reaction zone, then further sent to the XTO reaction zone and finally all the one or more catalysts of the XTO reaction zone is sent to the catalyst regeneration zone.

5. The process of claim 1, wherein all of the one or more catalysts from the catalyst regeneration zone is sent to the OC reaction zone, then further sent to the XTO reaction zone and finally at least a portion of the one or more catalysts of the XTO reaction zone is sent to the catalyst regeneration zone and the remaining portion of the one or more catalysts is sent to the OC reaction zone.

6. The process of claim 1, wherein all of the one or more catalysts from the catalyst regeneration zone is sent to the OC reaction zone, at least part of the one or more catalysts from the OC reaction zone is further sent to the XTO reaction zone and the remaining part of the one or more catalysts is sent to the catalyst regeneration zone and all of the one or more catalysts from the XTO is sent to the OC reaction zone.

7. The process of claim 1, wherein the OC reaction zone effluent is sent to a separation section and the light olefins are recovered, and wherein the hydrocarbons having 4 carbon atoms or more are recycled at an inlet of the OC reaction zone.

8. The process of claim 7, further comprising mixing the hydrocarbons having 4 carbon atoms or more recycled at the inlet of the OC reaction zone with the hydrocarbons having 4 carbon atoms or more recovered from the XTO reaction zone effluent.

9. The process of claim 7, wherein before recycling the hydrocarbons having 4 carbon atoms or more at the inlet of the OC reaction zone, the hydrocarbons having 4 carbon atoms or more are sent to a second fractionator to purge heavies.

10. The process of claim 1, wherein the OC reaction zone effluent and the XTO reaction zone effluent are mixed and sent to a fractionator, or separately sent to the same fractionator, where the light olefins are recovered and at least a portion of the hydrocarbons having 4 carbon atoms or more are recycled at an inlet of the OC reaction zone.

11. The process of claim 10, wherein before recycling the hydrocarbons having 4 carbon atoms or more at the inlet of the OC reaction zone, the hydrocarbons having 4 carbon atoms or more are sent to a second fractionator to purge heavies.

12. The process of claim 1, wherein ethylene is recycled over the OC reaction zone and wherein the ethylene can either come from a separation section of the XTO reaction zone, from a separation section of the OC reaction zone, from both the separation section of the XTO reaction zone and the separation section of the OC reaction zone, or from a common recovery section.

13. The process of claim 1, wherein ethylene is recycled over the XTO reaction zone and wherein the ethylene can either come from a separation section of the XTO reaction zone, from a separation section of the OC reaction zone, from both the separation section of the XTO reaction zone and the separation section of the OC reaction zone, or from a common recovery section.

14. The process of claim 1, wherein feed at an inlet in the OC reaction zone comprises a paraffin content of at least 20 wt % on a carbon basis.

15. The process of claim 1, wherein the light olefins comprises ethylene, which is further polymerized.

16. The process of claim 15, wherein the ethylene is further polymerized with one or more comonomers.

17. The process of claim 1, wherein the light olefins comprises propylene, which is further polymerized.

18. The process of claim 17, wherein the propylene is further polymerized with one or more comonomers.

19. The process of claim 1, wherein the one or more catalysts leaving the OC reaction zone and flowing to the XTO reaction zone contains at least 0.1% carbon.

20. The process of claim 1, wherein the feedstock is a halogenide-containing or sulphur-containing organic feedstock.

21. The process of claim 12, wherein at least a portion of the ethylene that is recycled over the OC reaction zone is converted into propylene.

22. The process of claim 1, wherein the one or more catalysts is a mixture of two or more catalysts and optionally a binder.

23. The process of claim 1, wherein the steaming is performed at a temperature ranging from 480 to 760° C.

24. The process of claim 1, wherein the one or more catalysts is a single catalyst.

25. The process of claim 1, wherein each of the one or more catalysts comprise the P-modified zeolite.

26. The process of claim 1, wherein the XTO reaction zone has a propylene yield of greater than 40%.

* * * * *